(12) United States Patent
Imai et al.

(10) Patent No.: US 10,517,618 B2
(45) Date of Patent: Dec. 31, 2019

(54) MEDICAL DEVICE AND TREATMENT METHOD

(71) Applicant: TERUMO KABUSHIKI KAISHA, Shibuya-ku, Tokyo (JP)

(72) Inventors: Masaomi Imai, Hadano (JP); Yuuki Masubuchi, Hadano (JP); Takashi Kitaoka, Hadano (JP); Takahiro Chida, Hadano (JP); Kazuaki Kanamoto, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 245 days.

(21) Appl. No.: 15/428,581

(22) Filed: Feb. 9, 2017

(65) Prior Publication Data

US 2017/0224364 A1 Aug. 10, 2017

(30) Foreign Application Priority Data

Feb. 10, 2016 (JP) .................. 2016-023809

(51) Int. Cl.
*A61B 17/22* (2006.01)
*A61B 17/221* (2006.01)

(52) U.S. Cl.
CPC ............ *A61B 17/22* (2013.01); *A61B 17/221* (2013.01); *A61B 2017/22038* (2013.01); *A61B 2017/22054* (2013.01); *A61B 2017/22079* (2013.01)

(58) Field of Classification Search
CPC . A61B 17/22; A61B 17/221; A61B 17/12027; A61B 17/12022; A61B 2017/22038; A61B 2017/22054; A61B 2017/22079; A61B 2017/22001; A61M 29/00
USPC ......................................... 606/191, 194, 198
See application file for complete search history.

(56) References Cited

U.S. PATENT DOCUMENTS

| | | | |
|---|---|---|---|
| 8,562,637 B2 | 10/2013 | Kusleika | |
| 2006/0041269 A1* | 2/2006 | Horrigan | A61B 17/12036 606/198 |
| 2011/0213403 A1* | 9/2011 | Aboytes | A61F 2/013 606/194 |

* cited by examiner

*Primary Examiner* — Tuan V Nguyen
(74) *Attorney, Agent, or Firm* — Buchanan Ingersoll & Rooney PC

(57) ABSTRACT

A medical device to be inserted into a body lumen to obstruct flow in the body lumen includes a shaft unit; a proximal slider and a distal slider that are slidable along the shaft unit; a first expanding member including a distal portion coupled to the proximal slider and a proximal portion coupled to the shaft unit; a second expanding member including a distal portion coupled to the distal slider and a proximal portion coupled to the proximal slider; and a cover that surrounds an outer periphery of the first expanding member and coupled to the proximal portion of the first expanding member, the cover being tubular and flexibly deformable independently of the first expanding member.

15 Claims, 17 Drawing Sheets

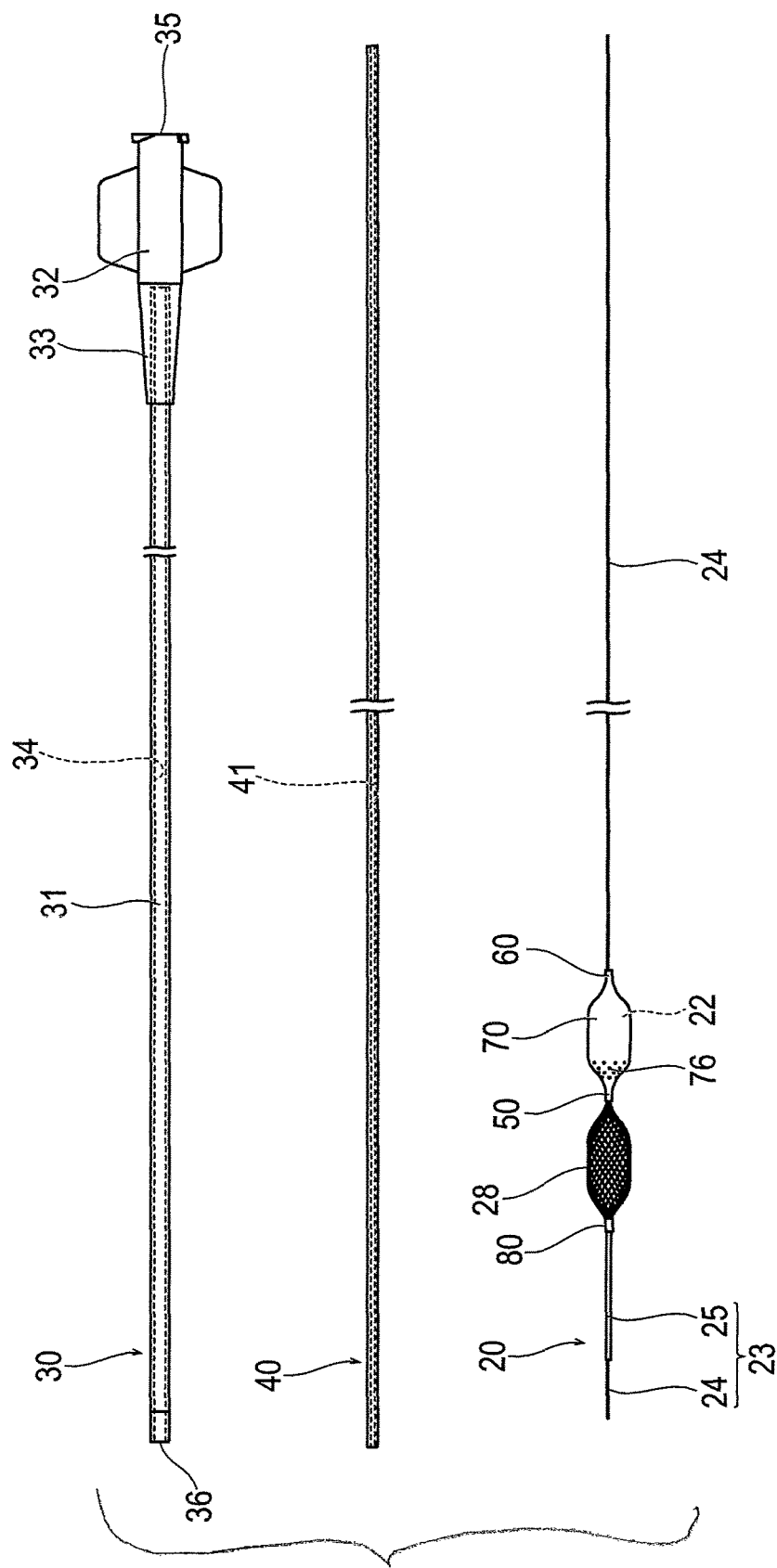

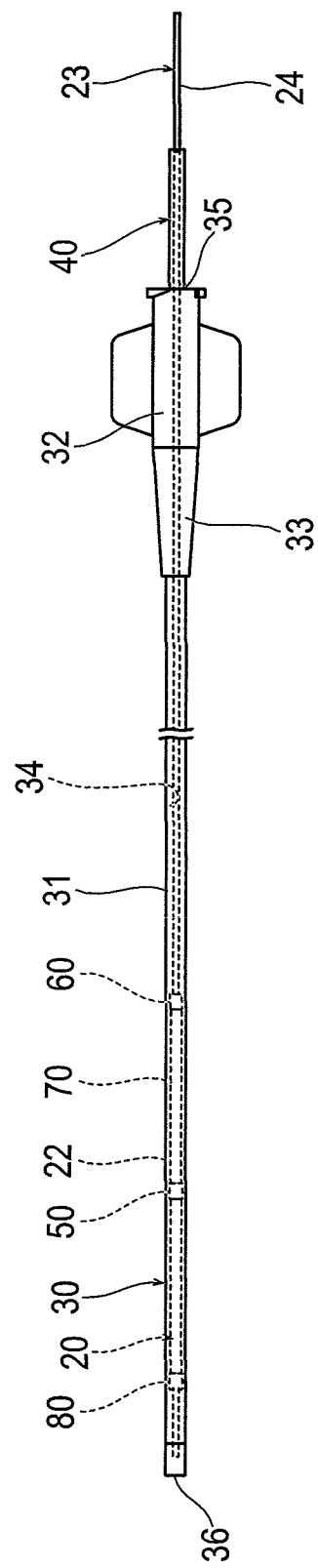

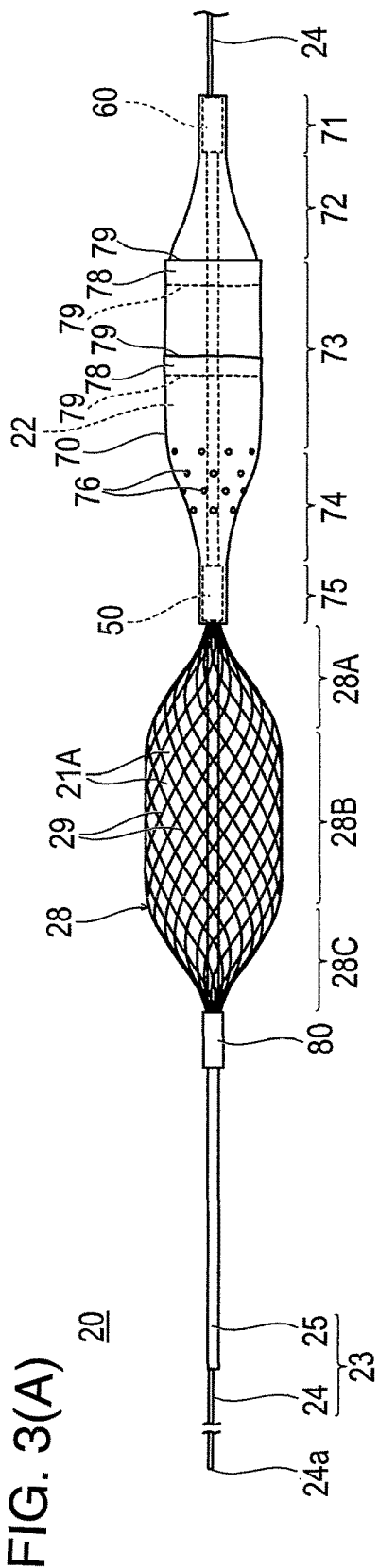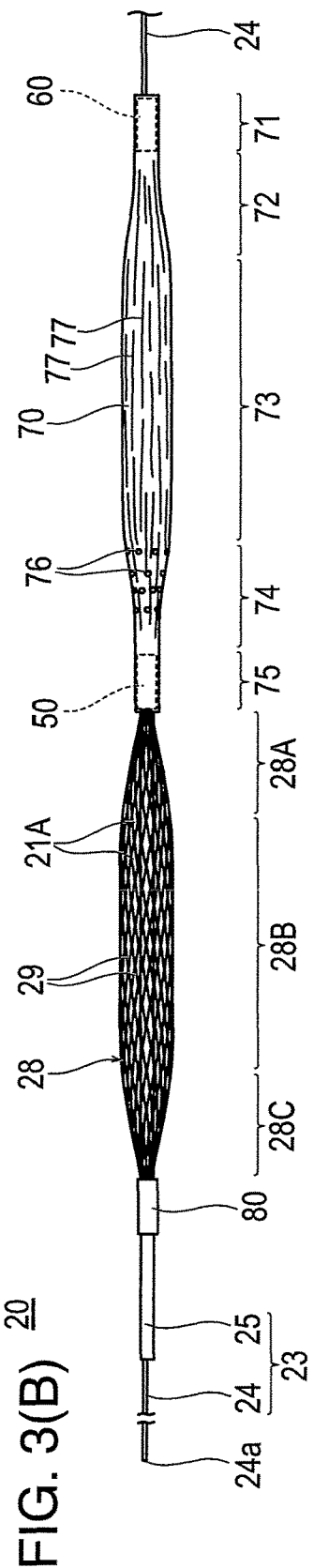

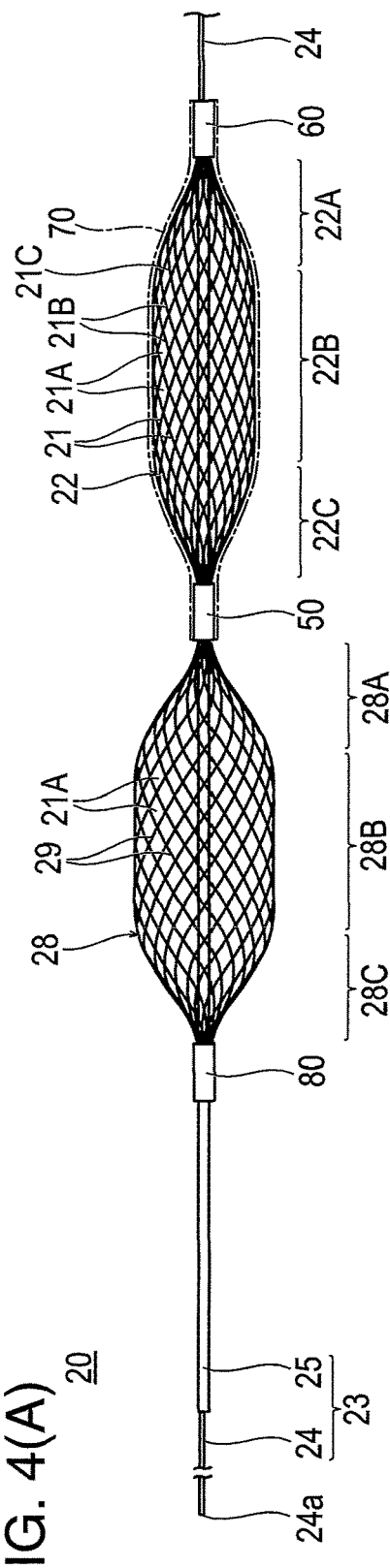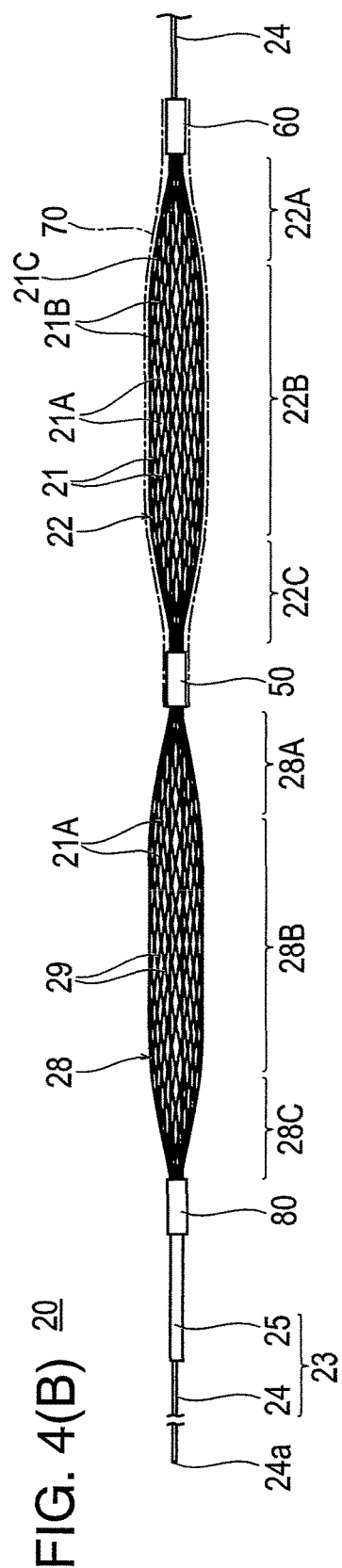
FIG. 4(A)
FIG. 4(B)

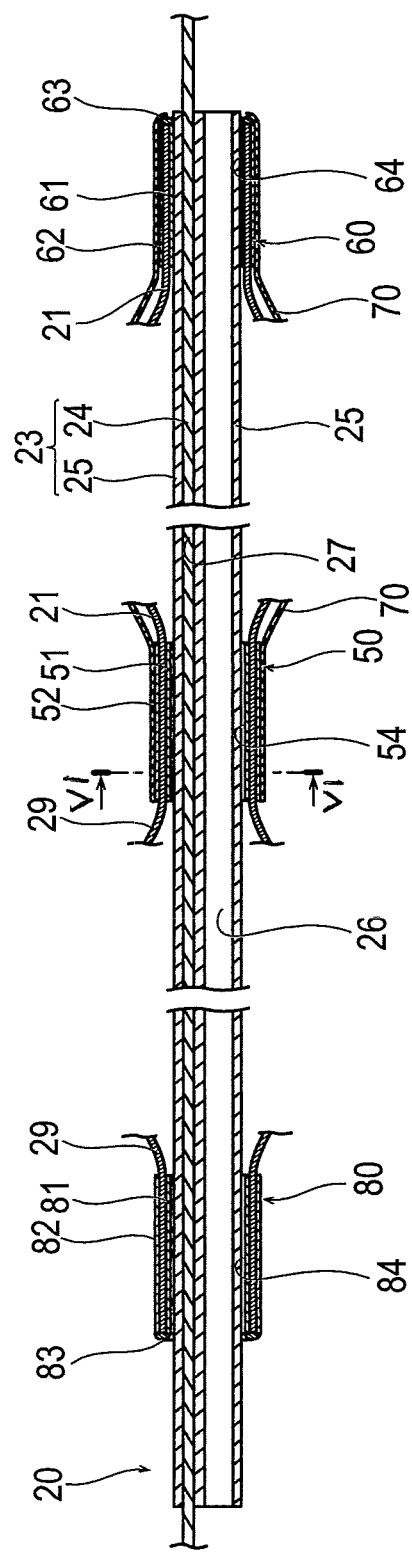

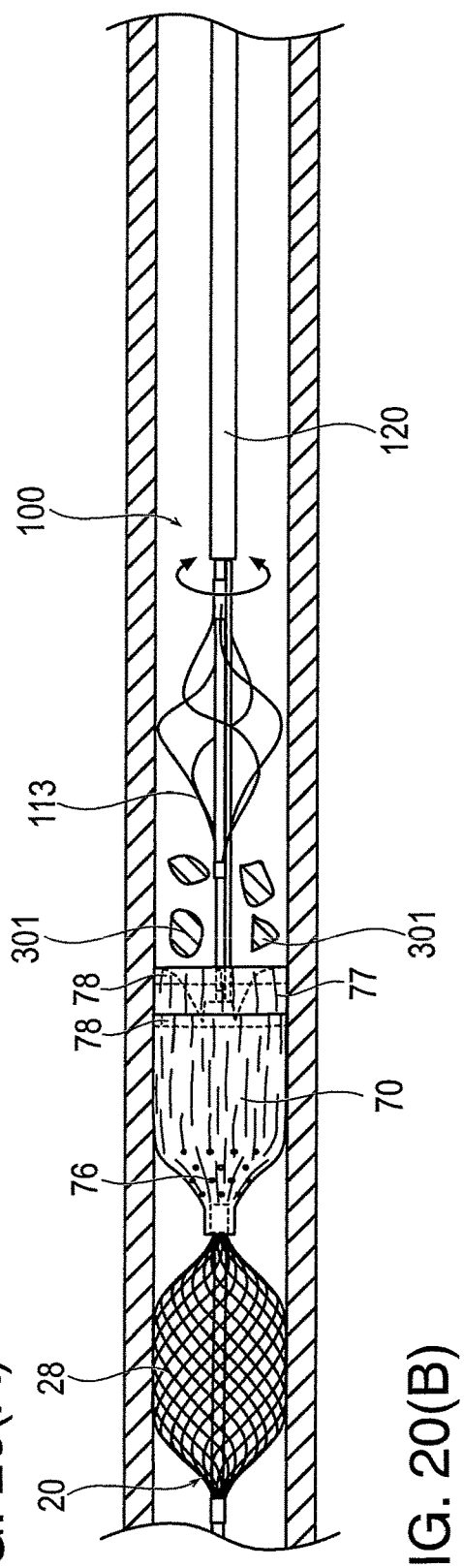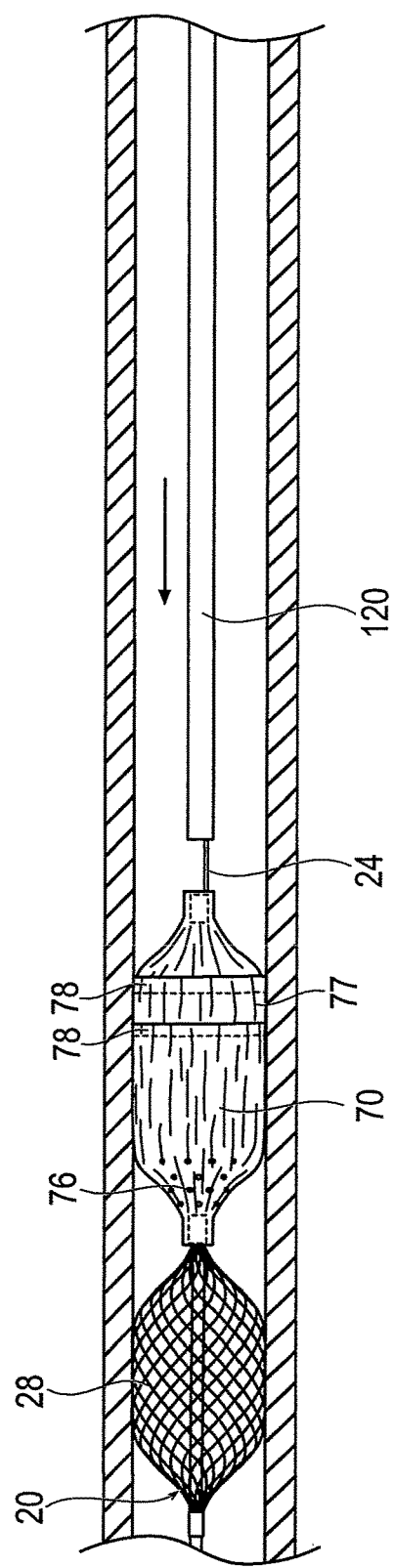

MEDICAL DEVICE AND TREATMENT METHOD

This application claims priority to Japanese Application No. 2016-023809 filed on Feb. 10, 2016, the entire content of which is incorporated herein by reference.

TECHNOLOGICAL FIELD

The present invention generally relates to a medical device and a treatment method used to remove an object from a body lumen.

BACKGROUND DISCUSSION

A thrombus formed in a portion of a vein, for example, may cause pain or swelling, and this may be treated by removing the thrombus with a thrombus-removing device that is percutaneously inserted into the vein. In such a treatment, if the entirety or a portion of the thrombus that has been separated from the wall of the blood vessel is carried by blood flow and reaches the lungs, there is a risk that pulmonary embolism will occur. Therefore, when such a treatment is performed, a thrombolytic agent is used before, during, and/or after the treatment, or the separated thrombus is removed as thoroughly as possible by suction during the treatment. However, even when these processes are carried out, there is still a possibility that a separated thrombus that is dangerously large from a clinical point of view will reach, for example, the lungs.

A filter that collects thrombi that flow through a blood vessel, for example, may be used to avoid pulmonary embolism (see, for example, U.S. Pat. No. 8,562,637). The filter, which has a mesh structure, is inserted into a blood vessel in a contracted state and expanded in the blood vessel.

It is difficult to collect small thrombi with the filter described in U.S. Pat. No. 8,562,637 because the mesh openings widen as the filter expands in the blood vessel. It is also difficult to suck the thrombi collected by the filter because the thrombi need to be sucked against strong blood flow.

SUMMARY

The medical device and treatment method disclosed here make it possible to obstruct flow in a body lumen (lumen in a living body) to enable effective removal of a substance from the body lumen, and the medical device is configured to be appropriately secured in the body lumen.

According to one aspect of the disclosure, a medical device to be inserted into a body lumen to obstruct flow in the body lumen comprises: an elongated shaft; a proximal slider slidably coupled to the elongated shaft so that the proximal slider is slidable along the elongated shaft; a distal slider slidably coupled to the elongated shaft so that the distal slider is slidable along the elongated shaft and so that the distal slider is located distal of the proximal slider, and first and second expanding members. The first expanding member is an elastically deformable tube including a plurality of through openings, wherein the first expanding member includes a distal portion coupled to the proximal slider and a proximal portion coupled to the elongated shaft. The tube includes a central portion possessing an outer diameter greater than an outer diameter of both end portions of the tube in a natural state in which no force is applied to the first expanding member. The second expanding member is also an elastically deformable tube including a plurality of through openings, wherein the second expanding member includes a distal portion coupled to the distal slider and a proximal portion coupled to the proximal slider. The tube of the second expanding member includes a central portion having an outer diameter greater than an outer diameter of both end portions of the tube of the second expanding member in the natural state in which no force is applied to the second expanding member. A cover surrounds the outer periphery of one of the first and second expanding members and is coupled to the proximal portion of the one of the first and second expanding members, to the proximal slider located further toward a proximal side than the proximal portion of the one of the first and second expanding members, or to the elongated shaft, with the cover being tubular and flexibly deformable independently of the one of the first and second expanding members.

Another aspect involves a medical device sized to be inserted into a body lumen to obstruct liquid flow in the body lumen, wherein the medical device comprises: an elongated shaft; a first expanding member comprised of an expandable and contractable first tube configured to be radially outwardly expanded and radially inwardly contracted, with the expandable and contractable first tube including a plurality of through openings. The expandable and contractable first tube includes end portions at opposite axial ends of the expandable and contractable first tube, with the elongated shaft passing through the expandable and contractable first tube so that the end portions of the expandable and contractable first tube surround the elongated shaft, and with at least one of the end portions of the expandable and contractable first tube being axially movable relative to the elongated shaft. The expandable and contractable first tube includes a central portion possessing an outer diameter greater than an outer diameter of both end portions of the expandable and contractable first tube in a natural state in which no force is applied to the expandable and contractable first tube. A second expanding member is configured to be radially outwardly expanded into contact with the inner surface of the body lumen and radially inwardly contracted out of contact with the inner surface of the body lumen, and the expandable and contractable second tube includes a plurality of through openings. The expandable and contractable second tube includes end portions at opposite axial ends of the expandable and contractable second tube, and the elongated shaft passes through the expandable and contractable second tube so that the end portions of the expandable and contractable second tube surround the elongated shaft, with at least one of the end portions of the expandable and contractable second tube being axially movable relative to the elongated shaft. The expandable and contractable second tube including a central portion possessing an outer diameter greater than the outer diameter of both end portions of the expandable and contractable second tube in a natural state in which no force is applied to the expandable and contractable second tube. The central portion of the expandable and contractable first tube and the central portion of the expandable and contractable second tube are axially spaced apart from one another. A cover surrounds the outer periphery of the central portion of the expandable and contractable first tube so that when the expandable and contractable first tube is radially outwardly expanded, the cover is outwardly expanded into contact with the inner surface of the body lumen to obstruct liquid flow past the expandable and contractable first tube. The central portion of the expandable and contractable second tube is devoid of any cover.

According to another aspect, a method comprises introducing first and second expanding members into a body lumen in a body while the first and second expanding members are located inside and covered by a sheath, with the second expanding member being surrounded by a cover; and pushing the first and second expanding members and the cover out of the sheath so that the first and second expanding members are positioned downstream of a lesion in the body lumen and causing the first and second expanding members to expand outwardly due to an elastic force of the first and second expanding members so that an outer surface of the first expanding member contacts an inner wall surface of the body lumen while the second expanding member, which is surrounded by the cover, presses the cover against the inner wall surface of the body lumen. The method also involves breaking up or dissolving an object generated in the lesion in the body lumen, inserting a removing device into the body lumen after breaking up or dissolving the object generated in the lesion in the body lumen and sucking-up the object using the removing device; causing the first and second expanding members and the cover to contract; and removing the medical device from the body lumen.

According to the above-described medical device and method, when the two expanding members and the cover are moved out of the sheath, one of the expanding members expands due to the elastic force thereof so as to press the cover against the inner wall surface of the body lumen, and the other expanding member, which is not surrounded by the cover, expands due to the elastic force thereof so as to come into contact with the inner wall surface of the body lumen. Accordingly, the medical device is capable of obstructing flow in the body lumen with the cover, and can be appropriately secured to the body lumen because the expanding member that is not surrounded by the cover and does not easily slip relative to the body lumen comes into contact with the inner wall surface of the body lumen. In the medical device, the expanding member that presses the cover against the inner wall surface of the body lumen to obstruct flow and the expanding member that is not surrounded by the cover and that is secured to the body lumen are provided as separate components, and therefore the structures of the expanding members can be optimized in accordance with the functions thereof. Accordingly, flow in the body lumen can be effectively obstructed and the medical device can be appropriately secured to the body lumen.

BRIEF DESCRIPTION OF THE DRAWINGS

FIG. 1 is a plan view of a medical device according to an embodiment.

FIG. 2 is a plan view of the medical device according to the embodiment illustrating the state in which an expanding unit, a pressing shaft, and a sheath are assembled.

FIGS. 3A and 3B are plan views of a distal portion of the expanding unit, wherein FIG. 3A illustrates the state in which expanding members are expanded and FIG. 3B illustrates the state in which the expanding members are contracted.

FIGS. 4A and 4B are transparent views of the distal portion of the expanding unit in which a cover is drawn transparently, wherein FIG. 4A illustrates the state in which the expanding members are expanded and FIG. 4B illustrates the state in which the expanding members are contracted.

FIG. 5 is an enlarged cross-sectional view of a proximal coupling member, a proximal slider, and a distal slider;

FIGS. 10A and 10B are cross-sectional views showing the inside of a blood vessel, wherein FIG. 10A illustrates the state in which the medical device is inserted in the blood vessel and FIG. 10B illustrates the state in which a second expanding member is expanded in the blood vessel.

FIGS. 11A and 11B are cross-sectional views showing the inside of the blood vessel, wherein FIG. 11A illustrates the state in which a first expanding member and the cover are expanded in the blood vessel and FIG. 11B illustrates the state in which the sheath and the pressing shaft are removed from the blood vessel.

FIGS. 14A and 14B are cross-sectional views showing the inside of the blood vessel, wherein FIG. 14A illustrates the state in which the removing device is inserted in the blood vessel and FIG. 14B illustrates the state in which a stirring unit of the removing device is expanded.

FIGS. 20A and 20B are cross-sectional views showing the inside of the blood vessel, wherein FIG. 20A illustrates the state in which thrombus fragments that have adhered to the expanding unit are being sucked and FIG. 20B illustrates the state in which the stirring unit is disposed in an outermost sheath member;

FIGS. 21A and 21B are cross-sectional views showing the inside of the blood vessel, wherein FIG. 21A illustrates the state in which the removing device is removed from the blood vessel and FIG. 21B illustrates the state in which the expanding members and the cover are disposed in the sheath.

DETAILED DESCRIPTION

Figure 6:
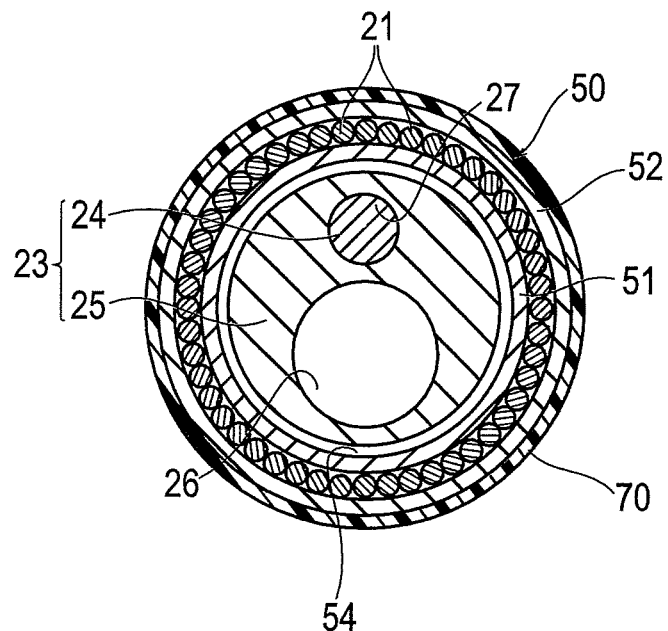
FIG. 6 is a sectional view taken along the section line VI-VI in FIG. 5.

Set forth below with reference to the accompanying drawings is a detailed description of an embodiment of a medical device and treatment method representing examples of the inventive medical device and treatment method disclosed here. In the drawings, dimensional ratios may be exaggerated and differ from the actual dimensional ratios to facilitate an understanding of the disclosed device and method.

A medical device 10 according to an embodiment representing one example of the disclosed medical device is used to obstruct flow in a blood vessel in order to remove an object, such as a thrombus or a plaque, from the blood vessel. In this specification, the side of the device from which the device is inserted into the blood vessel is referred to as the "distal side", and the side of the device at which the device is operated is referred to as the "proximal side". The object to be removed is not necessarily limited to a thrombus or a plaque, and may be any object that can exist in a body lumen (lumen in a living body). In this specification, the source side of the flow of blood in the blood vessel is referred to as the "upstream side", and the destination side of the flow of blood is referred to as the "downstream side".

As illustrated in FIGS. 1 and 2, the medical device 10 includes an expanding unit 20 that obstructs the flow of blood in a blood vessel, a sheath 30 configured to accommodate the expanding unit 20, and a pressing shaft 40 for pushing the expanding unit 20 out of the sheath 30. To obstruct the flow of blood means to regulate or impede (stop or reduce) the blood flow by closing or narrowing the cross section of the blood vessel, wherein the cross section is perpendicular to the axis of the blood vessel.

As illustrated in FIGS. 3A and 3B and FIGS. 4A and 4B, the expanding unit 20 includes a first expanding member 22 and a second expanding member 28, which are elastically deformable tubes having a mesh structure and which both include a plurality of through openings 21A; a cover 70 that surrounds the outer periphery of the first expanding member 22; and an elongated shaft unit 23 (elongated shaft) that extends axially or longitudinally through the first expanding member 22 and the cover 70. The expanding unit 20 also includes a proximal coupling member 60, which secures the first expanding member 22 to the shaft unit 23; a proximal slider 50, which is slidable relative to the shaft unit 23 and to which a distal portion of the first expanding member 22 and a proximal portion of the second expanding member 28 are secured; and a distal slider 80, which is slidable relative to the shaft unit 23 and to which a distal portion of the second expanding member 28 is secured.

As illustrated in FIGS. 1, 5 and 6, the shaft unit 23 includes an elongated wire 24 and a guidewire tube 25, which is secured to a distal portion of the wire 24 and in which a guidewire lumen 26 is formed. The guidewire tube 25 is secured to an inner peripheral surface 64 of an inner tube 61 provided on a proximal portion of the first expanding member 22. The guidewire tube 25 has a wire through hole 27, through which the wire 24 extends and to which the wire 24 is secured. The wire through hole 27 is parallel to the guidewire lumen 26. An end 24a of the wire 24 does not necessarily project from the guidewire tube 25 toward the distal side (distal end), and may be secured to, for example, the inner peripheral surface 64 of the inner tube 61 provided on the proximal portion of the first expanding member 22. The wire 24 and the guidewire tube 25 of the shaft unit 23, which are separate components, may instead be integrated together.

The material used to fabricate the wire 24 included in the shaft unit 23 is not particularly limited. For example, stainless steel or a shape memory alloy is preferably used. The material used to fabricate the guidewire tube 25 included in the shaft unit 23 is also not particularly limited. For example, a plastic material, such as a polyimide or a polyamide, stainless steel, or a shape memory alloy is preferably used.

As illustrated in FIGS. 4A and 4B, the first expanding member 22 includes a plurality of wires 21 that are flexibly deformable and braided into a mesh structure that forms a tube having the openings 21A. The proximal portion of the first expanding member 22 is secured to the proximal coupling member 60, and the distal portion of the first expanding member 22 is secured to the proximal slider 50.

The first expanding member 22 is deformable between an expanded state illustrated in FIG. 4A in which the outer diameter of the first expanding member 22 is increased due to the elastic force (restoring force) of the wires 21 in a natural state in which no force (no external force) is applied to the first expanding member 22, and a contracted state (diameter-reduced state) illustrated in FIG. 4B in which the outer diameter of the first expanding member 22 is reduced as a result of elastic deformation. In the natural state, owing to the structure in which the first expanding member 22 is surrounded by the cover 70, the first expanding member 22 expands so that the outer diameter of the first expanding member 22 does not become greater than or equal to the inner diameter of the cover 70 (second diameter-reduced state). The first expanding member 22 includes a proximal tapered portion 22A, which is tapered so that the inner and outer diameters of the proximal tapered portion 22A of the first expanding member 22 increase from the proximal portion toward the distal side (distal end); a central expanding portion 22B, which is located on the distal side of the proximal tapered portion 22A and has a substantially constant outer diameter; and a distal tapered portion 22C, which is tapered so that the inner and outer diameters of the distal tapered portion 22C of the first expanding member 22 decrease from the central expanding portion 22B toward the distal side (distal end). The central expanding portion 22B is a portion that expands so as to press the cover 70 against the inner wall of the blood vessel. When the first expanding member 22 is not covered with the cover 70, the maximum outer diameter of the first expanding member 22 in the expanded state (diameter-increased state) in which the first expanding member 22 is expanded due to the elastic force of the first expanding member 22 is greater than the maximum inner diameter of the cover 70. The first expanding member 22 is in a first diameter-reduced state when disposed in the sheath 30. The first expanding member 22 is in the second diameter-reduced state when expanded in the blood vessel so that the diameter of the first expanding member 22 is less than the maximum inner diameter of the cover 70 and further expansion is limited by the blood vessel. The first expanding member 22 is in a third diameter-reduced state when expanded in the cover 70 so that the outer diameter of the first expanding member 22 reaches a maximum outer diameter to which the diameter can be increased in the cover 70 and further expansion is limited by the cover 70. The outer diameter of the first expanding member 22 is largest in the diameter-increased state, second largest in the third diameter-reduced state, third largest in the second diameter-reduced state, and smallest in the first diameter-reduced state.

As illustrated in FIG. 5, the proximal coupling member 60 includes the inner tube 61 disposed inside the wires 21, an outer tube 62 disposed outside the wires 21, and a bonding portion 63 that bonds the inner tube 61 and the outer tube 62 together at the ends of the inner and outer tubes 61, 62. The wires 21 are sandwiched and secured between the inner tube 61 and the outer tube 62. The guidewire tube 25 is fixed to the inner tube 61 of the proximal coupling member 60. The bonding portion 63 may be omitted if the wires 21 can be fastened without the bonding portion 63. The proximal coupling member 60 may instead be slidably coupled to the shaft unit 23. More specifically, the proximal coupling member 60 may be rotatably coupled to the guidewire tube 25 or coupled to the guidewire tube 25 so as to be slidable within a predetermined range in the axial direction. The proximal coupling member 60 may be directly bonded to the shaft unit 23 or the tube 25. The proximal coupling member 60 is a member that is coupled to the wires 21 and the cover 70 on the shaft unit 23 or the tube 25. The coupled member may be only the inner tube 61, the outer tube 62, or the bonding portion 63. Alternatively, the coupled member may an adhesive. The proximal coupling member 60 may constitute a portion of the shaft unit 23 irrespective of whether the proximal coupling member 60 is secured to the shaft unit 23 or coupled to the shaft unit 23 so as to be slidable within a predetermined range.

As illustrated in FIGS. 5 and 6, the proximal slider 50 includes an inner tube 51 disposed inside the wires 21 and an outer tube 52 disposed outside the wires 21. The wires 21 are sandwiched and secured between the inner tube 51 and the outer tube 52. The guidewire tube 25 slidably extends through the inner tube 51. A gap 54 is provided between the inner tube 51 and the guidewire tube 25, so that the proximal slider 50 is movable along the guidewire tube 25 in the axial direction. The gap between the inner tube 51 and the guidewire tube 25 is not particularly limited, and is preferably 0.01 to 1.0 mm.

When the first expanding member 22 is in the expanded state, the proximal slider 50 slides along the guidewire tube 25 toward the proximal side (proximal direction or proximal end) so as to approach the proximal coupling member 60 (see FIGS. 3A and 4A). When the first expanding member 22 is in the contracted state, the proximal slider 50 slides along the guidewire tube 25 toward the distal side (distal direction or distal end) so as to move away from the proximal coupling member 60 (see FIGS. 3B and 4B). The outer diameter of the first expanding member 22, which has the braided structure, is changeable because the proximal slider 50 is movable toward and away from the proximal coupling member 60.

As illustrated in FIGS. 3A and 3B and FIGS. 4A and 4B, the second expanding member 28 includes a plurality of wires 29 that are flexibly deformable and braided into a mesh structure that forms a tube having the openings 21A. The proximal portion of the second expanding member 28 is secured to the proximal slider 50. The distal portion of the second expanding member 28 is secured to the distal slider 80. The wires 29 are the same as the wires 21 that form the first expanding member 22, and extend continuously from the wires 21. However, the wires 29 may instead be different from the wires 21.

The second expanding member 28 is deformable between an expanded state (see FIG. 4A) in which the outer diameter of the second expanding member 28 is increased due to the elastic force (restoring force) of the wires 29 in the natural state in which no force (no external force) is applied, and a contracted state (see FIG. 4B) in which the outer diameter thereof is reduced as a result of elastic deformation. The second expanding member 28 includes a proximal tapered portion 28A, which is tapered so that the inner and outer diameters of the proximal tapered portion 28A of the second expanding member 28 increase from the proximal portion of the second expanding member 28 toward the distal side (distal end or distal direction); a central expanding portion 28B, which is located on the distal side of the proximal tapered portion 28A and has a substantially constant outer diameter; and a distal tapered portion 28C, which is tapered so that the inner and outer diameters of the distal tapered portion 28C of the second expanding member 28 decrease from the central expanding portion 28B toward the distal side (distal end or distal direction). The central expanding portion 28B is a portion that expands so as to come into contact with the inner wall of the blood vessel. In the present embodiment, the second expanding member 28 has the same structure as the first expanding member 22 except that the second expanding member 28 is not surrounded by the cover 70 (the second expanding member 28 is uncovered). Therefore, when the second expanding member 28 is in the expanded state (diameter-increased state) in which the second expanding member 28 is expanded due to the elastic force of the second expanding member 28, the second expanding member 28 has a greater maximum outer diameter and a shorter length in the axial direction than the first expanding member 22 in the state in which expansion of the first expanding member 22 is limited by the cover 70. The shapes and structures of the first expanding member 22 and the second expanding member 28 may be set as appropriate in accordance with the functions thereof. In the present embodiment, the first expanding member 22 and the second expanding member 28 have the same structure except for the relationship between the first expanding member 22 and the cover 70. Since the first expanding member 22 is surrounded by the cover 70, when the first expanding member 22 and the second expanding member 28 are expanded, the first expanding member 22 and the second expanding member 28 have different shapes. The first expanding member 22 and the second expanding member 28 may instead have different structures. The second expanding member 28 may have an outer diameter greater than that of the first expanding member 22. In such a case, the second expanding member 28 can be reliably secured to the blood vessel. When the second expanding member 28 has a diameter greater than that of the first expanding member 22, the size of the mesh openings in the second expanding member 28 is smaller than that of the mesh openings in the first expanding member 22. Therefore, the second expanding member 28 reliably catches a thrombus. The first expanding member 22 may have an outer diameter greater than that of the second expanding member 28. In such a case, when the first expanding member 22 is located further toward the lungs than a thrombus (downstream of the thrombus) in the blood vessel, the first expanding member 22 reliably prevents blood and the thrombus from flowing toward the lungs. Since the first expanding member 22 stops blood flow in the blood vessel, the diameter of the blood vessel is reduced in the region closer to the lungs than the first expanding member 22 is (region downstream of the first expanding member 22). Therefore, even when the second expanding member 28 has an outer diameter smaller than that of the first expanding member 22, the second expanding member 28 can be strongly secured to the blood vessel. The second expanding member 28 is in a first diameter-reduced state when disposed in the sheath 30. The second expanding member 28 is in a second diameter-reduced state when expanded in the blood vessel and further expansion is limited by the blood vessel. The outer diameter of the second expanding member 28 is largest in the expanded state, second largest in the second diameter-reduced state, and smallest in the first diameter-reduced state.

As illustrated in FIG. 5, the distal slider 80 includes an inner tube 81 disposed inside the wires 29, an outer tube 82 disposed outside the wires 29, and a bonding portion 83 that bonds the inner tube 81 and the outer tube 82 together at the ends of the inner tube 81 and the outer tube 82. The wires 29 are sandwiched and secured between the inner tube 81 and the outer tube 82. The guidewire tube 25 slidably extends through the inner tube 81, and a gap is provided between the inner tube 81 and the guidewire tube 25, so that the distal slider 80 is movable along the guidewire tube 25 in the axial direction. The bonding portion 83 may be omitted if the wires 29 can be fastened by the inner tube 81 and the outer tube 82. The gap between the inner tube 81 and the guidewire tube 25 is not particularly limited, and is preferably 0.01 to 1.0 mm.

When the second expanding member 28 is in the expanded state, the distal slider 80 slides along the guidewire tube 25 toward the proximal side (proximal end or proximal direction) so as to approach the proximal slider 50 (see FIGS. 3A and 4A). When the second expanding member 28 is in the contracted state, the distal slider 80 slides along the guidewire tube 25 toward the distal side (distal end or distal direction) so as to move away from the proximal slider 50 (see FIGS. 3B and 4B). The outer diameter of the second expanding member 28, which has the braided structure, is changeable because the distal slider 80 is movable toward and away from the proximal slider 50.

The numbers of the wires 21 and 29 are not particularly limited, and may be, for example, 4 to 72. The braiding conditions of the wires 21 and 29 are not particularly limited.

The outer diameters of the wires 21 and 29 may be selected as appropriate in accordance with the materials of the wires 21 and 29 and the usage of the first expanding member 22 and the second expanding member 28, and may be, for example, 20 to 300 µm.

The wires 21 and 29 preferably include wires 21B and wires 21C having different outer diameters. The wires 21B have an outer diameter greater than that of the wires 21C. The wires 21B have an outer diameter of, for example, 200 µm, and the wires 21C have an outer diameter of, for example, 120 µm. In the present embodiment, two wires 21B and one wire 21C are alternately arranged (i.e., two of the larger outer diameters wires 21B are arranged next to a single one of the smaller outer diameter wires 21C, and this arrangement is repeated in an alternating manner), and sixteen wires 21B and eight wires 21C are used in total. Thus, one or two wires 21B and one or two wires 21C may be alternately arranged. When the first expanding member 22 and the second expanding member 28 include wires 21B and 21C having different outer diameters, in the state in which the first expanding member 22 and the second expanding member 28 are contracted and disposed in the sheath 30 (first diameter-reduced state), the smaller outer diameter wires 21C do not easily come into contact with the inner wall surface of the sheath 30 directly or indirectly through the cover 70. Accordingly, the intersecting points of the mesh are not easily displaced, and the first expanding member 22 and the second expanding member 28 have relatively high shape stability. In the case where the number of larger outer diameter wires 21B is greater than the number of smaller outer diameter wires 21C, the expanding force of the first expanding member 22 can be increased and the shape stability thereof can be increased accordingly. The number of larger outer diameter wires may be instead be smaller than or equal to the number of smaller outer diameter wires. In the case where the number of larger outer diameter wires is smaller than the number of smaller outer diameter wires, the expanding members are flexible and easily follow the shape of the body lumen. The first expanding member 22 and the second expanding member 28 may instead be formed of wires having the same outer diameter.

The wires 21 and 29 are preferably made of a flexible material. Preferred examples of the material include shape memory alloys to which shape memory properties and superelasticity are imparted by heat treatment, stainless steel, tantalum (Ta), titanium (Ti), platinum (Pt), gold (Au), tungsten (W), polyolefins such as polyethylene and polypropylene, polyamides, polyesters such as polyethylene terephthalate, fluorine-based polymers such as ethylene-tetrafluoroethylene copolymers (ETFE), polyether ether ketone (PEEK), and polyimides. Preferred examples of shape memory alloys include Ni—Ti-based alloys, Cu—Al—Ni-based alloys, Cu—Zn—Al-based alloys, and combinations thereof. A structure in which a plurality of materials are combined may be, for example, a structure in which a core made of Pt is coated with a Ni—Ti alloy or a core made of a Ni—Ti alloy is coated with gold to impart radiopacity.

The outer diameters of the outer tubes 52, 62, and 82 are not particularly limited, and may be, for example, 0.3 mm to 3.0 mm. The inner diameters of the inner tubes 51, 61, and 81 are not particularly limited, and may be, for example, 0.1 mm to 2.0 mm.

The materials of the inner tubes 51, 61, and 81 and the outer tubes 52, 62, and 82 are not particularly limited. For example, stainless steel or a shape memory alloy is preferably used.

The maximum outer diameter of the first expanding member 22 in the expanded state may be selected as appropriate in accordance with the inner diameter of the blood vessel, and may be, for example, 1 mm to 40 mm. The outer diameter of the first expanding member 22 in the contracted state may be selected as appropriate in accordance with the inner diameter of the blood vessel, and may be, for example, 0.3 mm to 4.0 mm. The length of the first expanding member 22 in the axial direction in the contracted state may be selected as appropriate in accordance with the blood vessel, and may be, for example, 20 mm to 150 mm.

As illustrated in FIGS. 3A and 3B, the cover 70 is a tubular member formed of a relatively thin film so as to cover the outer periphery of the entirety of the first expanding member 22. The cover 70 includes a cover proximal portion 71 fixed to the outer peripheral surface of the proximal coupling member 60 and a cover distal portion 75 fixed to the outer peripheral surface of the proximal slider 50. The cover 70 further includes a proximal tapered portion 72, which is tapered so that the inner and outer diameters of the proximal tapered portion 72 increase from the cover proximal portion 71 toward the distal side (distal end or distal direction); a cover central portion 73, which is located on the distal side of the proximal tapered portion 72 and has a substantially constant outer diameter; and a distal tapered portion 74, which is tapered so that the inner and outer diameters of the distal tapered portion 74 decrease from the cover central portion 73 toward the distal side. The cover distal portion 75 fixed to the outer peripheral surface of the proximal slider 50 may be omitted, and the cover 70 may have substantially constant inner and outer diameters on the distal side of the cover central portion 73.

Only the cover proximal portion 71 and the cover distal portion 75 of the cover 70 are fixed to the first expanding member 22; the proximal tapered portion 72, the cover central portion 73, and the distal tapered portion 74 simply cover the first expanding member 22 without being fixed to the first expanding member 22. Therefore, the portion of the cover 70 excluding both end portions is deformable independently of the first expanding member 22, and is configured to become separated from the first expanding member 22 so as not to be in contact with the first expanding member 22. Accordingly, the positions at which the first expanding member 22 and the cover 70 are in contact with each other differ between the expanded state and the contracted state. Since the cover 70 is deformable independently of the first expanding member 22, the wires 21 that form the first expanding member 22 are configured to change the crossing angle of the wires 21 without being obstructed by the cover 70, and the first expanding member 22 can be flexibly deformed. Since the crossing angle of the wires 21 changes when the outer diameter of the first expanding member 22 changes, the first expanding member 22 decreases in length in the axial direction as the outer diameter of the first expanding member 22 increases. In contrast, the cover 70 is formed of a relatively thin but strong material so that the cover 70 does not break, and the length of the cover 70 in the axial direction does not vary as easily as the first expanding member 22. The cover 70 may be coupled to the shaft unit 23 at a location on the proximal side of the proximal coupling member 60 instead of being coupled to the proximal coupling member 60. The cover 70 may include a film whose thickness is smaller than the diameter of the wires 21 and that is bonded between the wires 21 forming the mesh structure of the first expanding member 22 so as to cover the outer periphery of the entirety of the first expanding member 22. In this case, since the cover 70 is thinner than the wires 21, the first expanding member 22 and the cover 70 can be easily pulled back into the sheath 30.

As illustrated in FIG. 3B, when the cover 70 contracts, the diameter of the cover 70 decreases so that folded portions 77, which are folded so as to overlap themselves, are formed. The edges of the crease-shaped folded portions 77 extend in the axial direction. Multiple folded portions 77 are arranged in a circumferential direction. Preferably, the folded portions 77 are formed so that individual folds do not extend over the entire length of the cover 70 in the axial direction, and multiple folded portions 77 that are shorter than the entire length of the cover 70 in the axial direction are arranged at intervals in the axial direction. Each folded portion 77 may instead be formed so as to extend over the entire length of the cover 70 in the axial direction. A change in length of the cover 70 in the axial direction is smaller than that of the first expanding member 22. Therefore, the length of the cover 70 in the axial direction in the contracted state, in which the length of the first expanding member 22 in the axial direction is increased, is set so as to be the same as or slightly longer than that of the first expanding member 22. In this state, overlapping portions 78 (see FIG. 3A), which are folded so as to overlap themselves in the axial direction, are not formed on the cover 70.

As illustrated in FIG. 3A, when the cover 70 expands, the diameter of the cover 70 increases so that the folded portions 77 are unfolded and the overlapping area decreases. More specifically, the folded portions 77, which are folded so as to overlap themselves in the circumferential direction, are formed so as to bring the inner peripheral surface of the cover 70 into contact with itself, and are unfolded so that the outer diameter of the cover 70 changes. When the cover 70 is expanded, the folded portions 77 may remain partially folded instead of being completely unfolded. Since the length of the first expanding member 22 in the axial direction decreases in the expanded state, at least one or more overlapping portions 78, which are folded so as to overlap itself in the axial direction, may be formed on the cover 70 by using the excess length of the cover 70 in the axial direction in the expanded state. In the case where the diameter of the blood vessel is smaller than the maximum outer diameter of the first expanding member 22 in the natural state, the overlapping portions 78 may be formed so that one surface of each overlapping portion 78 is in contact with the inner wall of the blood vessel and the other surface of each overlapping portion 78 is in contact with the outer peripheral surface of the cover 70. To facilitate the formation of the overlapping portions 78, the cover 70 may be shaped in advance by applying heat while the cover 70 is folded at positions where the overlapping portions 78 are to be formed.

The distal tapered portion 74 of the cover 70 has at least one or more holes 76 formed therein. The holes 76 enable blood to enter the cover 70 when the cover 70 expands and the inner volume of the cover 70 increases, and discharge blood to the outside when the cover 70 contracts and the inner volume of the cover 70 decreases. Since the holes 76 are formed in the distal tapered portion 74, even when the cover central portion 73 is in contact with the inner wall surface of the blood vessel, the holes 76 are not blocked and blood appropriately flows into and out of the cover 70 through the holes 76. The diameter of the holes 76 is not particularly limited, and may be, for example, 0.1 mm to 2 mm.

The cover 70 obstructs blood flow so that a thrombus can be effectively removed from the blood vessel by suction by using a removing device 100 described below. Accordingly, preferably, no holes are formed at the proximal side of the cover 70 so that blood does not flow through the cover 70 from the proximal side to the distal side.

The maximum inner diameter of the cover 70 is smaller than the maximum outer diameter of the first expanding member 22 in the state in which the first expanding member 22 is expanded without being covered with the cover 70. Thus, the cover 70 surrounds the first expanding member 22 so as to forcibly suppress an increase in outer diameter of the first expanding member 22. Therefore, even when the cover 70 is in the expanded state, the first expanding member 22 can effectively exerts an expanding force. The maximum outer diameter of the cover central portion 73 of the cover 70 in the expanded state is greater than the inner diameter of the blood vessel, so that the cover central portion 73 is able to come into contact with the inner wall surface of the blood vessel.

The cover 70 may instead be formed of a highly elastic material so that the diameter of the cover 70 can be increased and reduced without forming the folded portions.

The maximum outer diameter of the cover central portion 73 of the cover 70 in the expanded state, which is greater than the inner diameter of the blood vessel, may be selected as appropriate in accordance with the blood vessel, and may be, for example, 1 mm to 40 mm. The maximum outer diameter of the cover 70 in the contracted state, which is smaller than the inner diameter of the blood vessel, may be selected as appropriate in accordance with the blood vessel, and may be, for example, 0.3 mm to 4.0 mm. The length of the first expanding member 22 in the axial direction in the contracted state may be selected as appropriate in accordance with the blood vessel, and may be, for example, 20 mm to 150 mm.

If the outer diameter of the cover 70 is too large, the storage space of the sheath 30 that accommodates the cover 70 becomes insufficient, and the resistance generated when the cover 70 is moved into or out of the sheath 30 increases. Therefore, the outer diameter of the cover 70 is preferably as small as possible.

If the cover 70 is too long in the axial direction, the storage space of the sheath 30 that accommodates the cover 70 becomes insufficient, and the resistance generated when the cover 70 is moved into or out of the sheath 30 increases. Therefore, the length of the cover 70 is preferably as small as possible.

The cover 70 is preferably made of a material that is relatively thin, that is strong so that the cover 70 does not break even when it is deformed, and that has a small frictional resistance so that the cover 70 can slide in the sheath 30. For example, polyethylene may be used. The thickness of the cover 70 is not particularly limited, and may be, for example, 5 to 30 μm.

It is not necessary that the cover 70 be formed of a film-shaped member, and may instead be formed of, for example, a mesh-shaped membrane or a braided body formed by braiding wires.

The inner surface of the cover 70 may be coated with a silicone resin, a fluorine-based resin such as Teflon (registered trade mark), a hydrophilic polymer, etc., to improve slidability. The hydrophilic polymer may be, for example, poly(hydroxyethyl methacrylate), poly(hydroxyethyl acrylate), hydroxypropyl cellulose, a methyl vinyl ether-maleic anhydride copolymer, polyethylene glycol, polyacrylamide, or polyvinylpyrrolidone. When the slidability of the inner surface of the cover 70 is improved, the cover 70 can be easily pulled (retracted) into the sheath 30 after being expanded in the blood vessel. The treatment for improving the slidability may be performed not only on the inner peripheral surface of the cover 70 but also on the outer peripheral surface of portions of the cover 70 excluding the cover central portion 73, which is required to exert a contact force on the wall of the blood vessel. In such a case, the cover 70 can be more easily pulled into the sheath 30 after being expanded in the blood vessel.

As illustrated in FIGS. 1 and 2, the sheath 30 includes a sheath tube 31, a hub 32, and an anti-kink protector 33. The sheath tube 31 includes a lumen 34 configured to accommodate the expanding unit 20. The lumen 34 opens in a tube opening 36 (open distal end), which is formed in a distal end portion of the sheath tube 31. The hub 32 is secured to a proximal end portion of the sheath tube 31, and includes a hub opening 35 that communicates with the lumen 34. The anti-kink protector 33 is a flexible member that covers the coupling portion between the sheath tube 31 and the hub 32, and prevents kinking of the sheath tube 31.

The material of the sheath tube 31 is not particularly limited. Preferred examples of the material include polyolefins such as polyethylene, polypropylene, ethylene-propylene copolymers, and ethylene-vinyl acetate copolymers, polyvinyl chloride, polystyrene, polyamides, polyimides, and combinations thereof. The sheath tube 31 may be made of a plurality of materials, and reinforcing members, such as wires, may be embedded therein.

The pressing shaft 40 is a tube that is configured to be disposed in the lumen 34 in the sheath 30. The pressing shaft 40 has a pushing lumen 41 formed therein, and the wire 24 of the expanding unit 20 is configured to be inserted into the pushing lumen 41. The inner diameter of the pushing lumen 41 is smaller than the outer diameter of the proximal coupling member 60 of the expanding unit 20. Therefore, the proximal coupling member 60 cannot be inserted into the pushing lumen 41. Accordingly, the pressing shaft 40 is capable of pressing the proximal coupling member 60 toward the distal side.

The material of the pressing shaft 40 is not particularly limited. Preferred examples of the material include polyolefins such as polyethylene, polypropylene, ethylene-propylene copolymers, and ethylene-vinyl acetate copolymers, polyvinyl chloride, polystyrene, polyamides, polyimides, and combinations thereof. The pressing shaft 40 may be made of a plurality of materials, and reinforcing members, such as wires, may be embedded therein.

The removing device 100, which is inserted into a blood vessel to remove a thrombus, will now be described.

Figure 7:
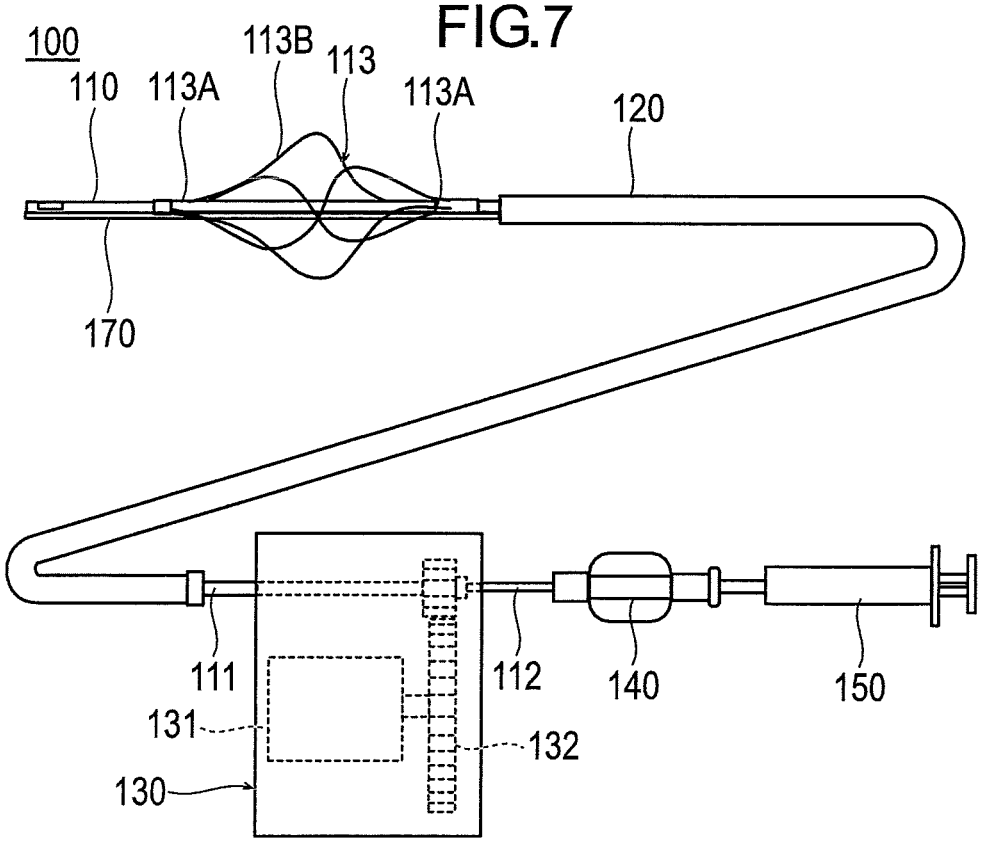
FIG. 7 is a plan view of a removing device.
Figure 8:
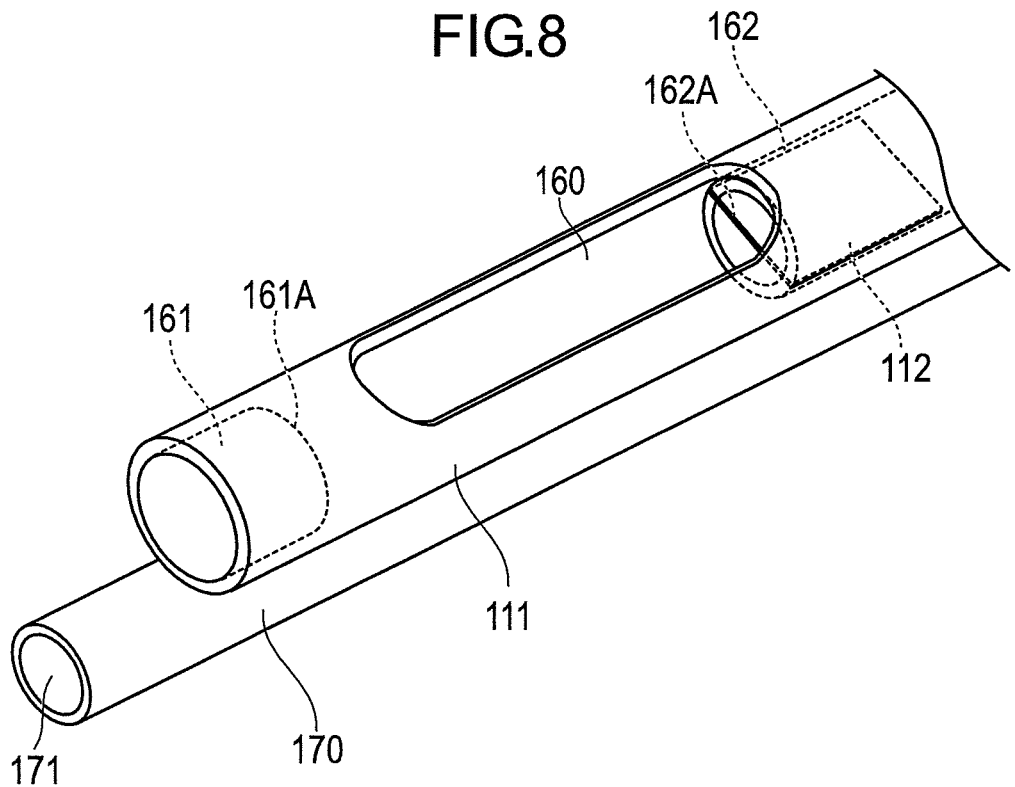
FIG. 8 is a perspective view of a distal portion of the removing device.
Figure 9:
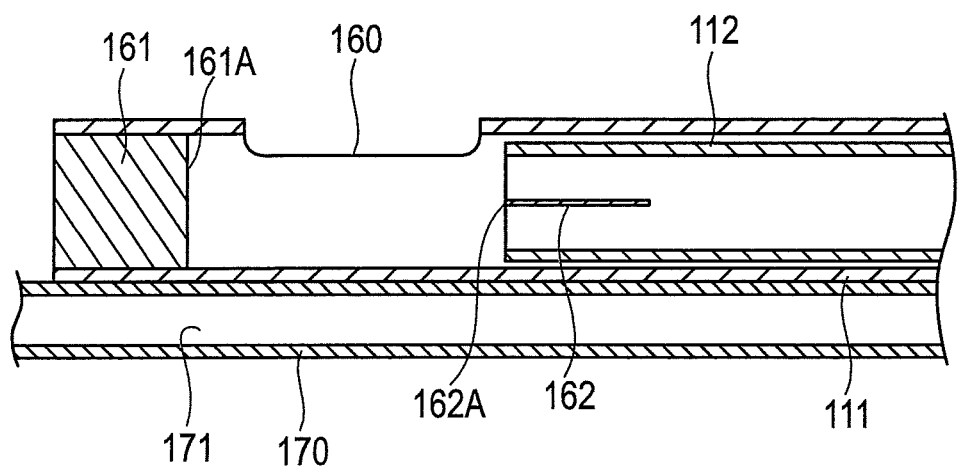
FIG. 9 is a sectional view of the distal portion of the removing device.

As illustrated in FIGS. 7 to 9, the removing device 100 includes an elongated shaft body 110; an outermost sheath member 120, in which the shaft body 110 is disposed and which is slidable relative to the shaft body 110 in the axial direction; and a guidewire tube 170 in which a second guidewire lumen 171 is formed. The removing device 100 further includes a rotary drive unit 130 configured to rotate the shaft body 110, a hub 140 provided on a proximal end portion of the shaft body 110, and a syringe 150 connected to the hub 140 at a proximal side of the hub 140.

The shaft body 110 includes a shaft outer tube 111 and a shaft inner tube 112, each of which has a hollow elongated shape. The shaft outer tube 111 and the shaft inner tube 112 each have a lumen therein. The inner diameter of the shaft outer tube 111 is greater than the outer diameter of the shaft inner tube 112, and the shaft inner tube 112 is disposed in the shaft outer tube 111. The shaft inner tube 112 is movable relative to the shaft outer tube 111 in the axial direction.

The shaft outer tube 111 includes a distal end portion that constitutes a distal portion of the shaft body 110, and a proximal end portion that is disposed in the rotary drive unit 130. The shaft inner tube 112 includes a proximal end portion that extends toward the proximal side (proximal end) beyond the proximal end portion of the shaft outer tube 111 and that is connected to the hub 140. The syringe 150, which is connected to the hub 140, is configured to set the pressure in the shaft inner tube 112 to a negative pressure by suction.

The guidewire tube 170 is fixed to the shaft outer tube 111 so as to extend along the shaft outer tube 111. The second guidewire lumen 171, through which a guidewire can be inserted, is formed in the guidewire tube 170.

The shaft outer tube 111 is made of a flexible material having properties that enable rotational driving force applied at the proximal side (proximal end) to be transmitted to the distal side (distal end). The shaft inner tube 112 is made of a flexible material having properties that enable back-and-forth reciprocating driving force applied at the proximal side (proximal end) to be transmitted to the distal side (distal end). The shaft outer tube 111 and the shaft inner tube 112 may each be formed of, for example, a tube having the shape of a multilayer coil, such as a three-layer coil having alternating winding directions of right, left, and right, or a material obtained by embedding a reinforcing member, such as wires, in a polyolefin such as polyethylene or polypropylene, a polyamide, a polyester such as polyethylene terephthalate, a fluorine-based polymer such as an ethylene-tetrafluoroethylene copolymer (ETFE), polyether ether ketone (PEEK), a polyimide, or a combination thereof.

The material of the outermost sheath member 120 is not particularly limited. Preferred examples of the material include polyolefins such as polyethylene and polypropylene, polyamides, polyesters such as polyethylene terephthalate, fluorine-based polymers such as ETFE, PEEK, and polyimides. The outermost sheath member 120 may be made of a plurality of materials, and reinforcing members, such as wires, may be embedded therein.

A stirring unit 113 is provided at a distal portion of the shaft outer tube 111. The stirring unit 113 includes two axially spaced-apart base portions 113A secured to the peripheral surface of the shaft outer tube 111 at proximal and distal locations. A plurality of spiral portions 113B extend between the base portions 113A. The spiral portions 113B are individually twisted in the same direction along the axial direction. The spiral portions 113B are secured to the two base portions 113A at different positions in the circumferential direction and curved at different positions in the axial direction. Accordingly, the stirring unit 113 is shaped so as to swell uniformly in the circumferential direction as a whole. When the shaft outer tube 111 rotates, the stirring unit 113 also rotates to break a thrombus in the blood vessel into fragments and stir the thrombus fragments.

The spiral portions 113B of the stirring unit 113 are formed of relatively thin flexible metal wires. The stirring unit 113 is disposed in the outermost sheath member 120 until the shaft body 110 is positioned at a target region. After the shaft body 110 has been positioned at the target region, the outermost sheath member 120 is slid toward the proximal side (proximal end or proximal direction) so that the stirring unit 113 is moved out of the outermost sheath member 120 so as to be uncovered and is expanded as illustrated in FIG. 7. Accordingly, the spiral portions 113B are preferably formed of a material having shape memory properties. Preferred examples of the material of the spiral portions 113B include shape memory alloys to which shape memory properties and superelasticity are imparted by heat treatment and stainless steel. Preferred examples of shape memory alloys include Ni—Ti-based alloys, Cu—Al—Ni-based alloys, Cu—Zn—Al-based alloys, and combinations thereof.

The rotary drive unit 130 includes a drive motor 131 and a gear unit 132 that connects the drive motor 131 to the shaft outer tube 111 of the shaft body 110. The shaft outer tube 111 can be rotated in the circumferential direction by rotating the drive motor 131. In the present embodiment, the shaft outer tube 111 is driven by the drive motor 131 so that the shaft outer tube 111 alternately rotates in positive and negative directions (one rotational direction and the opposite rotational direction) along the circumferential direction. When the shaft outer tube 111 alternately rotates in the positive and negative directions, the blood alternately flows alternately in opposite directions.

A through opening 160 having the shape of an elongated hole is formed in the shaft outer tube 111 so as to extend in the axial direction at a location near the distal portion of the shaft outer tube 111. Thus, the inside and outside of the shaft outer tube 111 communicate with each other by way of the through opening 160. A cylindrical attachment portion 161, which blocks the hollow inside of the shaft outer tube 111, is provided at the distal portion of the shaft outer tube 111. Thus, the distal portion of the shaft outer tube 111 is closed. The proximal surface of the attachment portion 161 serves as an attachment surface 161A that faces the distal surface (axially facing distal end surface) of the shaft inner tube 112. The attachment surface 161A is located further toward the distal side than a distal end portion of the opening 160 in the shaft outer tube 111. The attachment portion 161 is formed of, for example, stainless steel.

The distal end surface of the shaft inner tube 112 is located at the position of the proximal end portion of the opening 160 in the shaft outer tube 111 or further toward the proximal side than the proximal end portion of the opening 160. A cutting unit 162 (cutter) is disposed in the hollow inside of a distal end portion of the shaft inner tube 112. The cutting unit 162 is formed of a relatively thin metal plate, has a width corresponding to the diameter of the shaft inner tube 112, and includes a sharp blade 162A at the distal end of the cutting unit 162.

As illustrated in FIG. 8, the blade 162A and the shaft inner tube 112 are arranged so that no step is provided between the distal end surfaces thereof. That is, the distal-most end of the blade 162A and the distal-most end of the shaft inner tube 112 are axially aligned with one another. Therefore, when the distal surface of the shaft inner tube 112 comes into contact with the attachment surface 161A of the attachment portion 161, the blade 162A also comes into contact with the attachment surface 161A. The shaft inner tube 112 is configured to reciprocate relative to the shaft outer tube 111 in the axial direction at least between the position illustrated in FIG. 9 and the position at which the shaft inner tube 112 comes into contact with the attachment surface 161A of the attachment portion 161. The distal portion of the shaft inner tube 112 may have a thickness (difference between the inner and outer diameters of the inner tube) that is smaller than that of a portion of the shaft inner tube 112 other than the distal portion and equivalent to the thickness of the blade 162A of the cutting unit 162.

The blade 162A may instead be arranged such that the distal end surface of the blade 162A projects distally beyond the distal end surface of the shaft inner tube 112. The amount of projection is preferably 0.5 to 10 mm. In this case, the blade 162A effectively comes into contact with the attachment surface 161A of the attachment portion 161, and the cutting effect improves.

The shaft outer tube 111 and the shaft inner tube 112 are arranged coaxially with each other, and the rotary drive unit 130 is configured to reciprocate the shaft outer tube 111 in the circumferential direction. However, the shaft outer tube 111 is not limited to those capable of reciprocating, and may instead rotate in one direction. The cutting unit 162 is arranged so as to divide the cross section of the hollow inside of the shaft inner tube 112 into halves.

Next, a method of using the medical device 10 and the removing device 100 according to the present embodiment in order to, for example, remove a thrombus from a blood vessel by suction will be described.

First, an introducer sheath is percutaneously inserted into the blood vessel at a location upstream of a thrombus 300 (on the proximal or peripheral side of the thrombus 300) in the blood vessel. A guidewire 90 is inserted into the blood vessel through the introducer sheath. Then, the guidewire 90 is further inserted to a location on the distal side of the thrombus 300.

Next, as illustrated in FIG. 2, the medical device 10, in which the expanding unit 20 and the pressing shaft 40 are disposed in the sheath 30, is prepared. The first expanding member 22, the second expanding member 28, and the cover 70 are arranged at a location near the distal end portion of the sheath tube 31 of the sheath 30, and the shapes thereof are maintained in the contracted state. The shaft unit 23 projects from the hub opening 35 in the hub 32 toward the proximal side (in the proximal direction).

Figure 10:
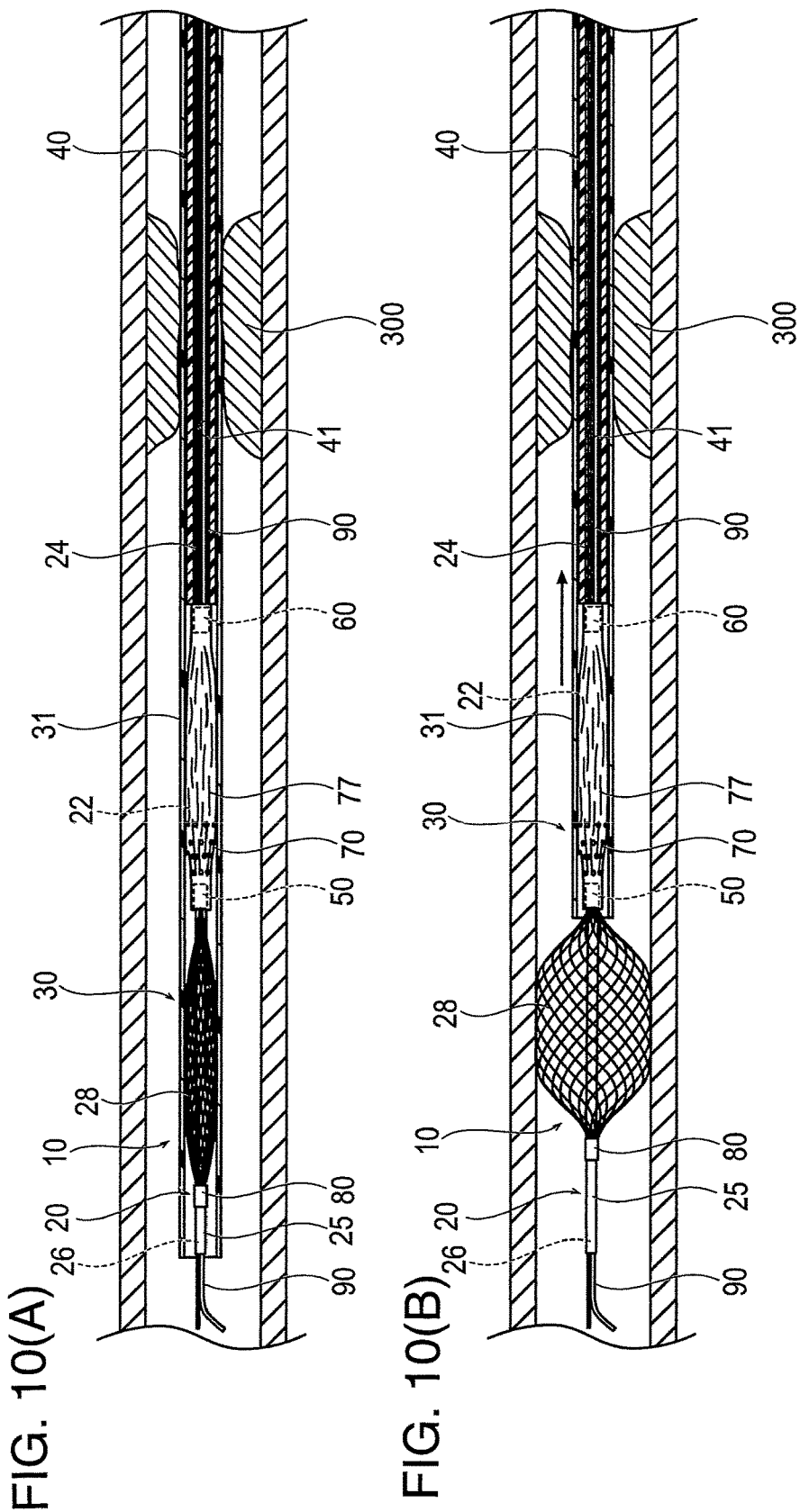

Next, the proximal end portion of the guidewire 90 that is located outside the body is inserted into the guidewire lumen 26 in the medical device 10, and the medical device 10 is advanced along the guidewire 90 to a location on the distal side of the thrombus 300, as illustrated in FIG. 10A. A separately prepared support catheter may be used to advance the guidewire 90 to the location on the distal side of the thrombus 300.

Next, the operator moves the sheath 30 toward the proximal side (in the proximal direction) while holding the pressing shaft 40 with his or her hand so that the pressing shaft 40 does not axially move. At this time, the distal end portion of the pressing shaft 40 is in contact with the proximal coupling member 60 or the proximal end portion of the guidewire tube 25, so that movement of the first expanding member 22 and the cover 70 is restrained. Accordingly, the position of the proximal portions of the first expanding member 22 and the cover 70 in the blood vessel can be freely adjusted. When the sheath 30 is moved toward the proximal side (in the proximal direction) relative to the pressing shaft 40, the second expanding member 28 moves out of the sheath tube 31 (i.e., is exposed outside the sheath tube 31). Accordingly, as illustrated in FIG. 10B, the second expanding member 28 expands to an optimum size due to the restoring force of the second expanding member 28 while the distal slider 80 moves toward the proximal slider 50. Thus, the second expanding member 28 comes into contact with the inner wall surface of the blood vessel. The second expanding member 28 has a mesh structure and is not covered with the cover 70. Therefore, the second expanding member 28 is pressed into the inner wall surface of the blood vessel and is strongly secured.

Figure 11:
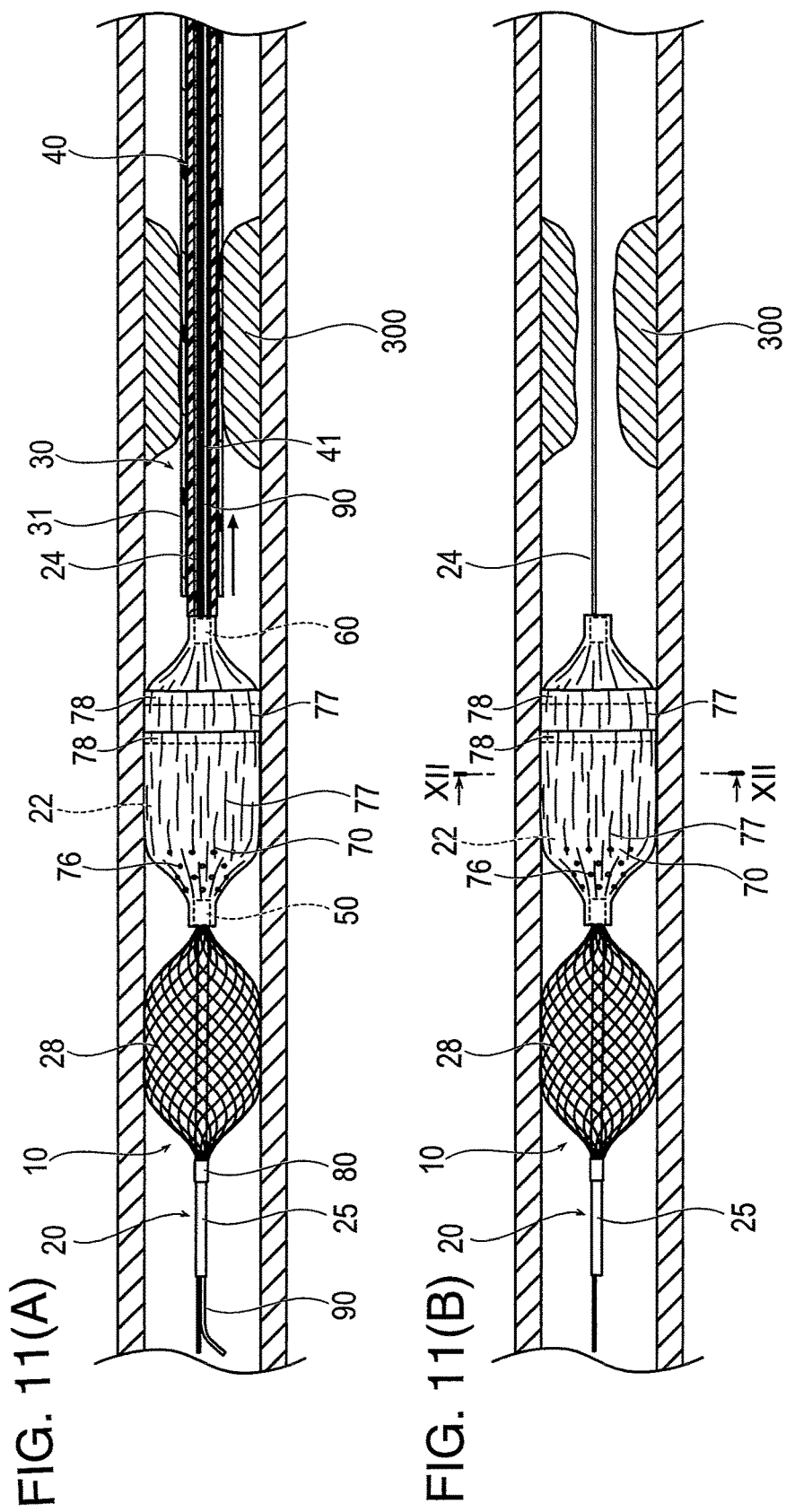
Figure 12:
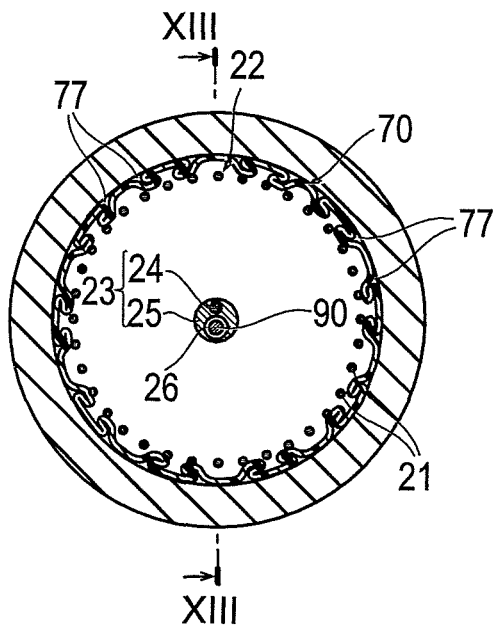
FIG. 12 is a cross-sectional view taken along line XII-XII in FIG. 11B.

Next, the operator further moves the sheath 30 toward the proximal side (in the proximal direction) while holding the pressing shaft 40 with his or her hand so that the pressing shaft 40 does not move. As a result, the first expanding member 22 and the cover 70 move out of the sheath tube 31. Accordingly, as illustrated in FIG. 11A, the first expanding member 22 expands to an optimum size due to the restoring force of the first expanding member 22 while the proximal slider 50 and the proximal coupling member 60 move relatively toward each other. When the first expanding member 22 expands, the cover 70 also expands and is pressed against the inner wall surface of the blood vessel. Since the second expanding member 28 has already been secured to the blood vessel by the time the first expanding member 22 expands, the proximal slider 50 hardly moves relative to the blood vessel. Therefore, preferably, the pressing shaft 40 is gradually pushed inward so that the proximal coupling member 60 moves toward the proximal slider 50. The folded portions 77 are unfolded and spread by the first expanding member 22 in accordance with the inner diameter and shape of the blood vessel, so that the cover 70 comes into contact with and is pressed against the inner wall surface of the blood vessel by the first expanding member 22. Even when the folded portions 77 remain folded in the state in which the cover 70 is in contact with the inner wall surface of the blood vessel, as illustrated in FIG. 12, the cover 70 is pressed against the inner wall surface of the blood vessel by the first expanding member 22, so that no gap is formed between the cover 70 and the inner wall surface of the blood vessel. Since the folded portions 77 provided on the cover 70 are short and arranged at intervals in the axial direction, small gaps formed between the folded portions 77 and the inner wall surface of the blood vessel are also arranged at intervals in the axial direction. Since the gaps are not formed so as to extend continuously in the axial direction of the cover 70, the cover 70 is capable of effectively obstructing the blood flow. The first expanding member 22 is disposed in the cover 70 in such a manner that an increase in diameter of the first expanding member 22 is forcibly suppressed by the cover 70. Therefore, the first expanding member 22 exerts a sufficient expanding force on the inner wall surface of the blood vessel not only when the outer diameter of the first expanding member 22 in the expanded state is small, but also when the outer diameter of the first expanding member 22 in the expanded state is large. Accordingly, the first expanding member 22 is applicable to blood vessels having a wide range of inner diameters.

When the first expanding member 22 expands in the radial direction, the length of the first expanding member 22 in the axial direction decreases. Therefore, the cover 70 becomes longer than the first expanding member 22 in the axial direction. At least one or more overlapping portions 78, which are folded in the axial direction, may be formed by using the excess length of the cover 70 in the axial direction in the expanded state.

The maximum diameter to which the first expanding member 22 being used can be expanded is greater than the diameter of the blood vessel into which the first expanding member 22 is inserted. Accordingly, the first expanding member 22 does not fully expand in the blood vessel, but exerts an expanding force so that the cover 70 is effectively brought into close contact with the wall of the blood vessel. Then, as illustrated in FIG. 11B, the sheath 30 and the pressing shaft 40 are pulled out of the body while the expanding unit 20 is left inside the body.

Figure 13:
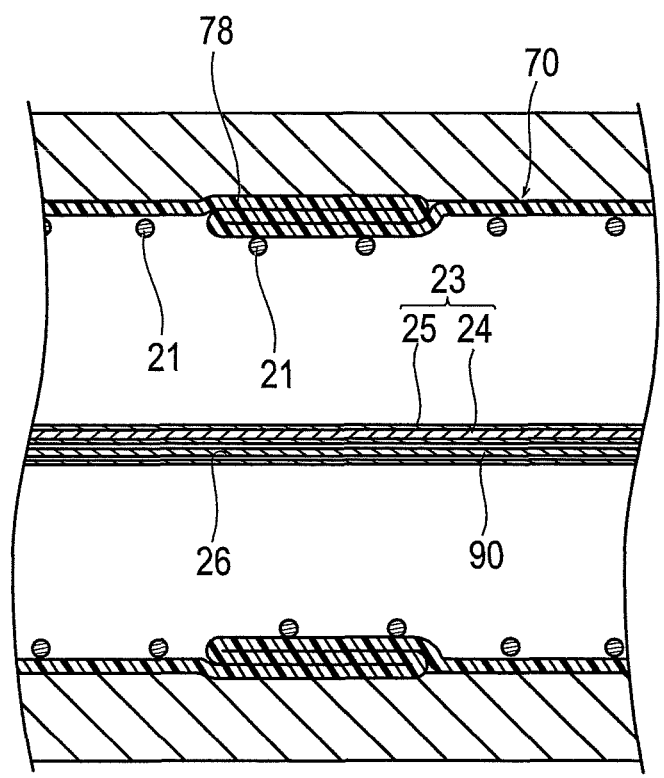
FIG. 13 is a cross-sectional view taken along line XIII-XIII in FIG. 12.

When the cover 70 is brought into close contact with the inner wall surface of the blood vessel by the expanding force exerted by the first expanding member 22, the blood flow in the blood vessel is stopped or reduced, so that the blood stagnates. A plurality of overlapping portions 78 are formed on the cover 70, so that the cover 70 increases in thickness and projects in the radial direction, as illustrated in FIG. 13, at locations where the overlapping portions 78 are formed. Thus, the overlapping portions 78 increase the effect of obstructing the blood flow through the space between the blood vessel and the cover 70. The overlapping portions 78 are formed so as to project toward the proximal side on the outer peripheral surface of the cover 70. Accordingly, the effect of obstructing the blood flow with the overlapping portions 78 can be further increased.

Figure 14:
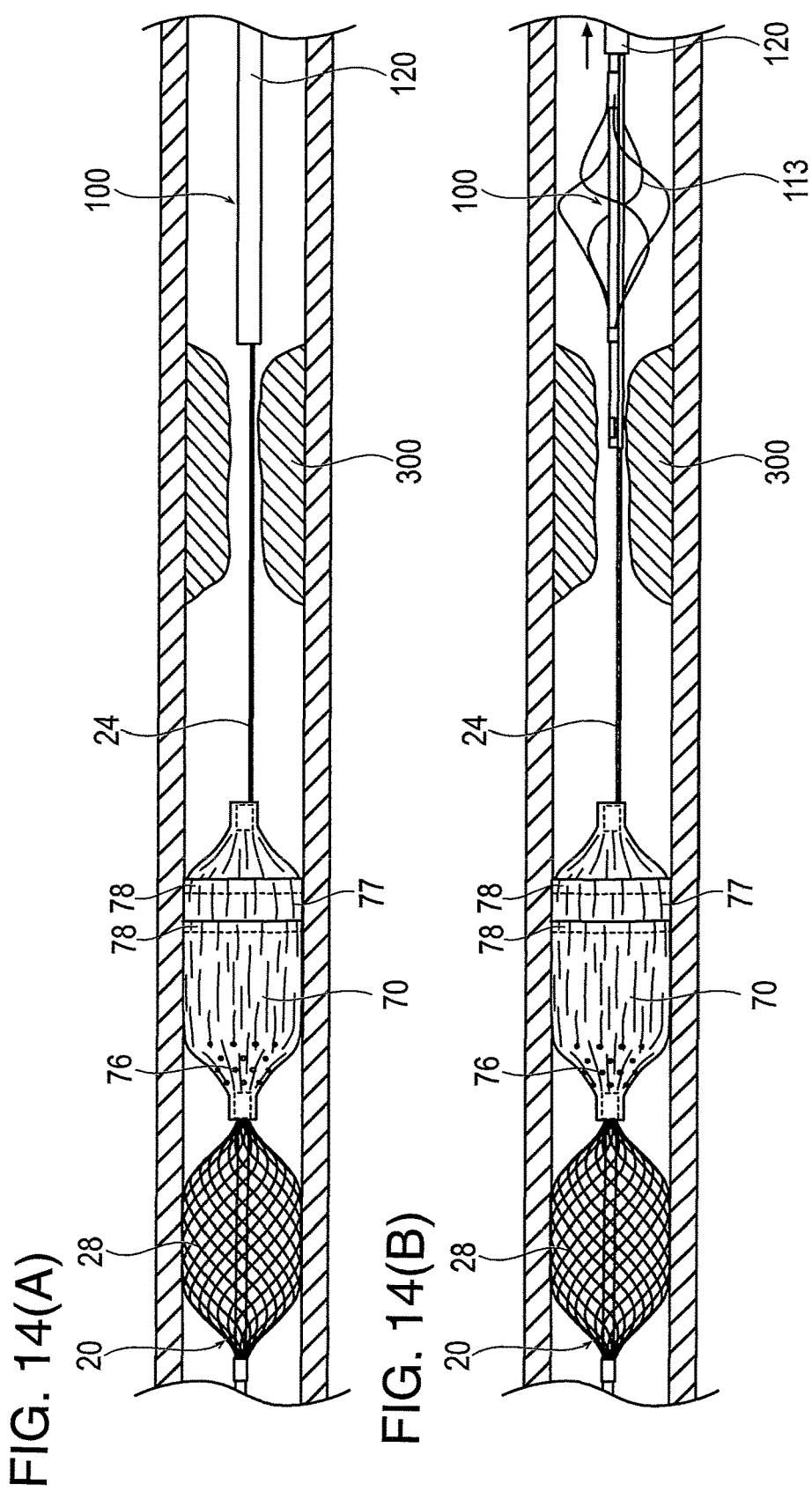

Next, the removing device 100 in the state in which the distal portion of the shaft body 110 including the stirring unit 113 is disposed in the outermost sheath member 120 is prepared. The proximal end portion of the wire 24 is inserted into the second guidewire lumen 171 (see FIG. 9) in the removing device 100. After this, as illustrated in FIG. 14A, the removing device 100 is axially advanced and positioned at a location on the proximal side of the thrombus 300 by using the wire 24 as a guide. After this, the outermost sheath member 120 is moved toward the proximal side (in the proximal direction), so that the stirring unit 113 is exposed and expands in the blood vessel, as illustrated in FIG. 14B.

Next, a thrombolytic agent is injected into the region around the thrombus 300 in the blood vessel by using the outermost sheath member 120, the shaft inner tube 112, or the second guidewire lumen 171 (see FIG. 9). At this time, since the blood flow in the region where the thrombus is formed is regulated (stopped or reduced), the density of the thrombolytic agent is maintained at a high level, and the effectiveness of the thrombolytic agent is increased. Here, it is not necessary that the thrombolytic agent be used.

Next, in the state in which the stirring unit 113 is positioned at a location near the thrombus 300, the shaft outer tube 111 is rotated by the rotary drive unit 130, so that the stirring unit 113 rotates and breaks up the thrombus 300 that has adhered to the inner wall surface of the blood vessel.

Figure 15:
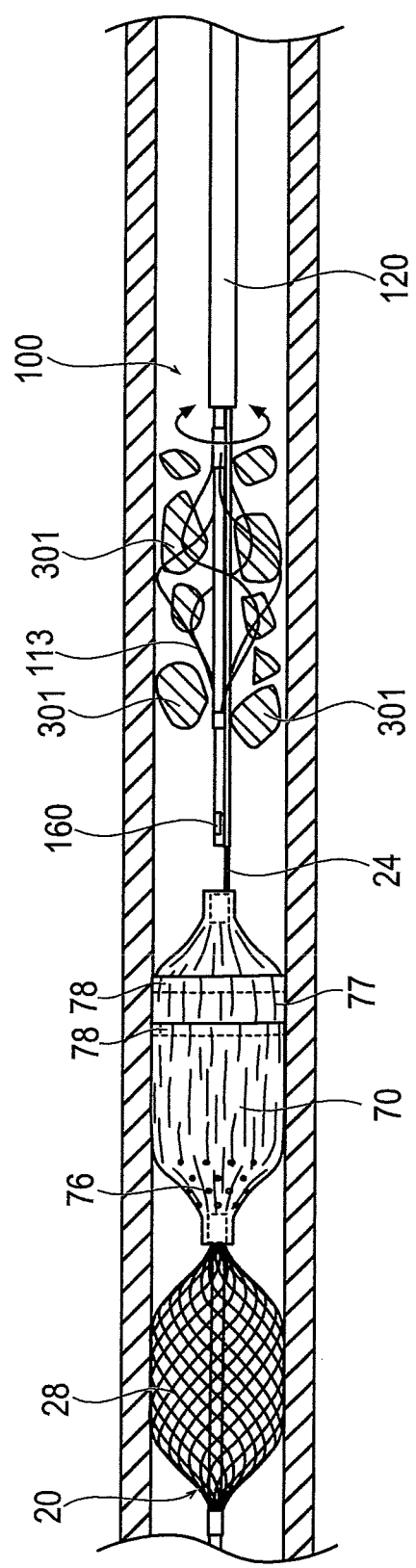
FIG. 15 is a cross-sectional view showing the inside of the blood vessel in the state in which a thrombus has been broken by the stirring unit.

When the stirring unit 113 is continuously rotated, since the blood flow is obstructed by the medical device 10, the entirety of the thrombus 300 that has adhered to the inner wall of the blood vessel is broken into thrombus fragments 301, as illustrated in FIG. 15. The thrombus fragments 301 do not, for example, precipitate in the blood vessel in which the blood is stagnant, but float in the blood vessel.

Figure 16:
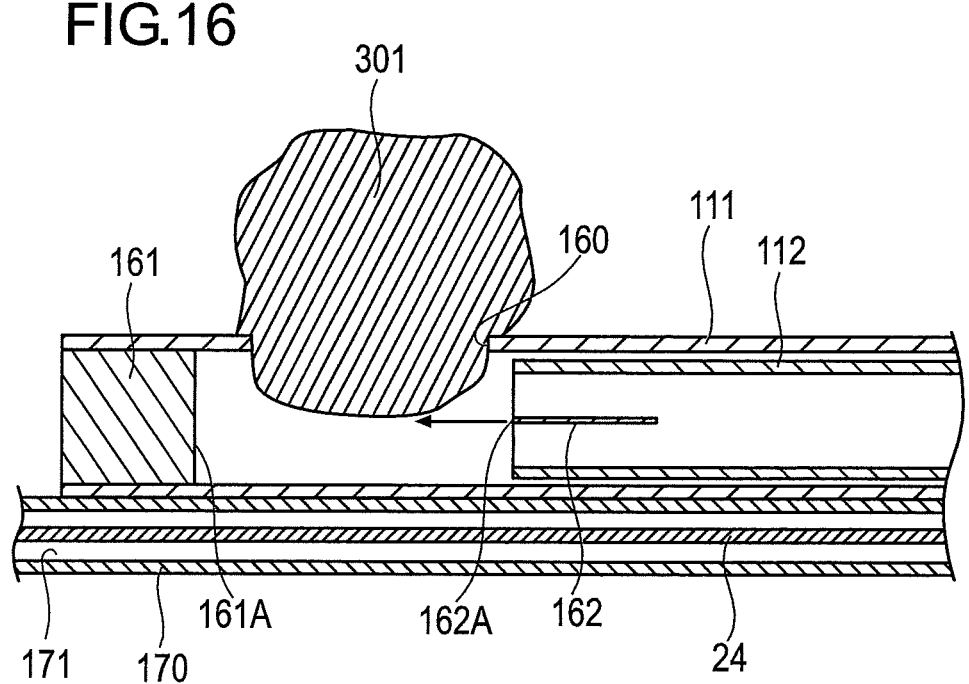
FIG. 16 is an enlarged cross-sectional view of the distal portion of the removing device illustrating the state in which a thrombus fragment is sucked into an opening in an outer tube.

Next, a plunger of the syringe 150 (see FIG. 7) is pulled to set the pressure in the shaft inner tube 112 to a negative pressure. The distal end portion of the shaft inner tube 112 communicates with the hollow inside of the shaft outer tube 111, and the shaft outer tube 111 communicates with the outside of the shaft body 110 through the opening 160. Accordingly, a suction force is applied to the outside of the shaft body 110 through the opening 160, so that the thrombus fragments 301 that float in the blood vessel are attracted to or drawn towards the opening 160. FIG. 16 illustrates a state in which one of the thrombus fragments 301 is attracted to the opening 160 and a portion of thrombus fragment 301 has entered the hollow inside of the shaft outer tube 111.

Figure 17:
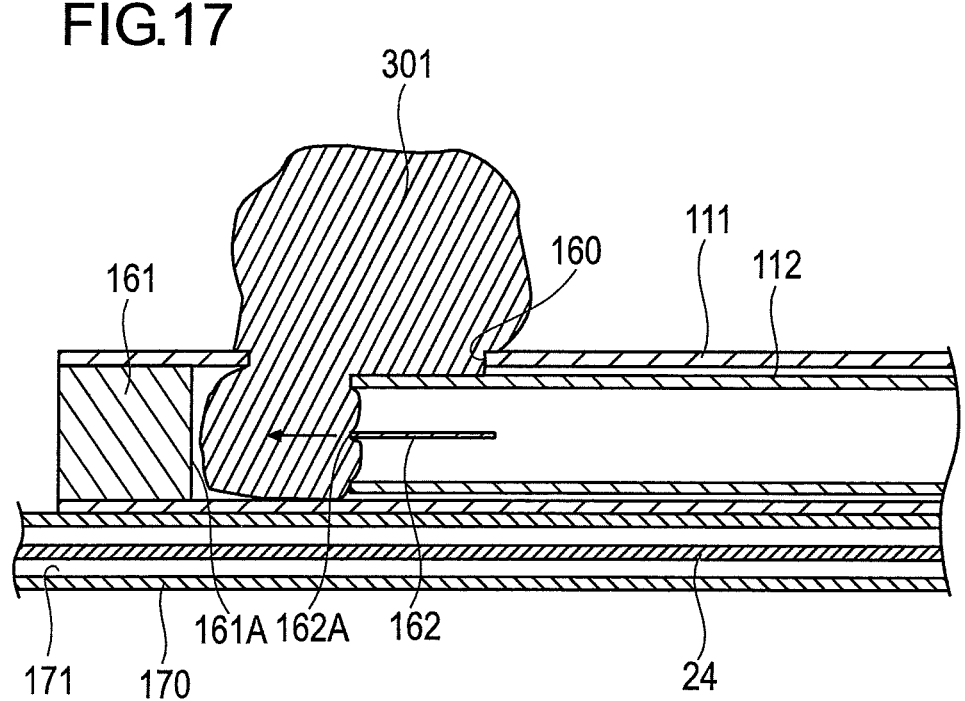
FIG. 17 is an enlarged cross-sectional view of the distal portion of the removing device illustrating the way in which the thrombus fragment that has been sucked into the opening in the outer tube is cut by the inner tube.

After the plunger of the syringe 150 has been pulled, the shaft inner tube 112 is moved relative to the shaft outer tube 111 in the axial direction. When the shaft inner tube 112 is moved from a location on the proximal side of the opening 160 toward the distal side (in the distal direction) of the shaft outer tube 111, that is, toward the attachment portion 161, as illustrated in FIG. 17, a portion of the thrombus fragment 301 that has entered the hollow inside of the shaft outer tube 111 through the opening 160 is cut while being compressed by the distal surface of the shaft inner tube 112.

Figure 18:
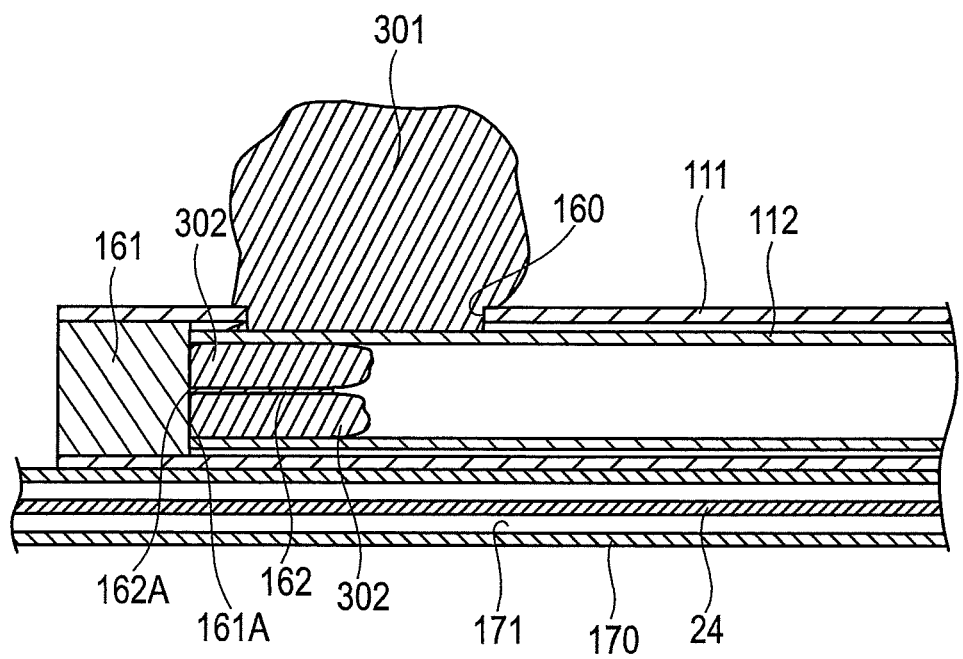
FIG. 18 is an enlarged cross-sectional view of the distal portion of the removing device illustrating the state in which a portion of the thrombus fragment that has been cut off by the inner tube is cut by a cutting unit.

When the shaft inner tube 112 is moved until the distal surface of the shaft inner tube 112 comes into contact with the attachment surface 161A of the attachment portion 161, as illustrated in FIG. 18, a thrombus fragment 302 that has been cut off remains in the hollow inside of the shaft inner tube 112. At this time, the thrombus fragment 302 is cut into two pieces by the blade 162A of the cutting unit 162 provided at the distal portion of the shaft inner tube 112. When the shaft inner tube 112 comes into contact with the attachment surface 161A of the attachment portion 161, the blade 162A also comes into contact with the attachment surface 161A. Accordingly, the thrombus fragment 302 that has been cut off in the hollow inside of the shaft outer tube 111 is cut by the blade 162A while being pressed against the attachment portion 161. Therefore, the thrombus fragment 302 that has been cut off can be reliably cut into pieces that are smaller than the inner diameter of the shaft inner tube 112. Thus, the occurrence of clogging of the hollow inside of the shaft inner tube 112 by the thrombus fragment 302 that has been cut off can be suppressed.

Figure 19:
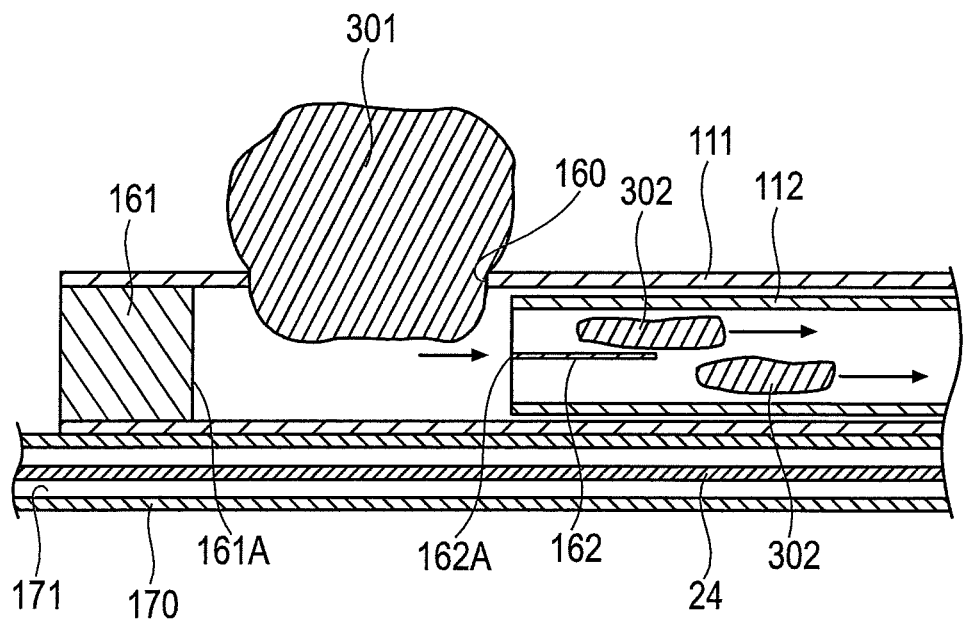
FIG. 19 is an enlarged cross-sectional view of the distal portion of the removing device illustrating the state in which the thrombus fragments that have been cut by the cutting unit are sucked toward a proximal side of the inner tube.

The hollow inside of the shaft inner tube 112 is continuously set to, or continuously maintained at, a negative pressure by the syringe 150. Therefore, as illustrated in FIG. 19, the pieces of the thrombus fragment 302 that has been cut off move toward the proximal side (proximal direction) through the hollow inside of the shaft inner tube 112. When the shaft inner tube 112 is moved away from the attachment portion 161 toward the proximal side (proximal direction), the opening 160 is opened again so that the thrombus fragment 301 is sucked into the hollow inside of the shaft outer tube 111. Thus, by repeatedly reciprocating the shaft inner tube 112 in the axial direction, the thrombus fragment 301 can be continuously cut into small pieces and sucked up.

When the thrombus fragment 301 is being cut, suction of the blood does not occur because the opening 160 is closed. This has an effect of reducing the amount of blood that is sucked up, which is preferably as small as possible.

The shaft outer tube 111 is preferably continuously rotated while the thrombus fragments 301 are being sucked by the shaft body 110. When the shaft outer tube 111 is rotated, the blood swirls in the blood vessel and the thrombus fragments 301 are relatively easily collected in the region around the rotational center, that is, in the region around the radial center of the blood vessel. Accordingly, the thrombus fragments 301 can be rather easily sucked through the opening 160. The swirling flow generated in the region around the opening 160 also affects the flow in the hollow inside of the shaft inner tube 112, and the swirling flow is also generated in the shaft inner tube 112. Accordingly, the flow resistance in the axial direction is reduced in the shaft inner tube 112, and the pieces of the thrombus fragment 302 that have been cut off can be smoothly sucked up.

In the present embodiment, while the thrombus fragments 301 are being sucked up, the shaft outer tube 111 is rotated and the shaft inner tube 112 is reciprocated relative to the shaft outer tube 111 in the axial direction. However, an additional movement may be performed. For example, the shaft inner tube 112 may be rotated so that the shaft inner tube 112 and the shaft outer tube 111 rotate relative to each other in different ways (in opposite rotation directions or in the same rotation direction at different rotation speeds). In such a case, the thrombus fragments 301 sucked into the opening 160 can be more reliably cut and guided through the hollow inside of the shaft outer tube 111. Furthermore, the shaft outer tube 111 may be reciprocated to break up the thrombus 300 and stir the thrombus fragments 301 in a larger region.

In the present embodiment, since the blood flow is obstructed by the medical device 10, the thrombus fragments 301 float in the blood that is stagnant and do not flow to a different location. The removing device 100 is configured to efficiently suck the thrombus fragments 301 through the opening 160 and removing the thrombus fragments 301 from the blood vessel. Although it would be necessary to apply a strong suction force if the blood was flowing, in the present embodiment, suction force can be more easily applied because the blood flow is obstructed. Accordingly, the thrombus fragments 301 can be effectively sucked up.

As illustrated in FIG. 20A, the thrombus fragments 301 may be sucked up while the removing device 100 is pressed against the cover 70 and the proximal portion of the cover 70 is pushed inward, so that the thrombus fragments 301 that have adhered to the cover 70 can be sucked through the opening 160.

Figure 21A:
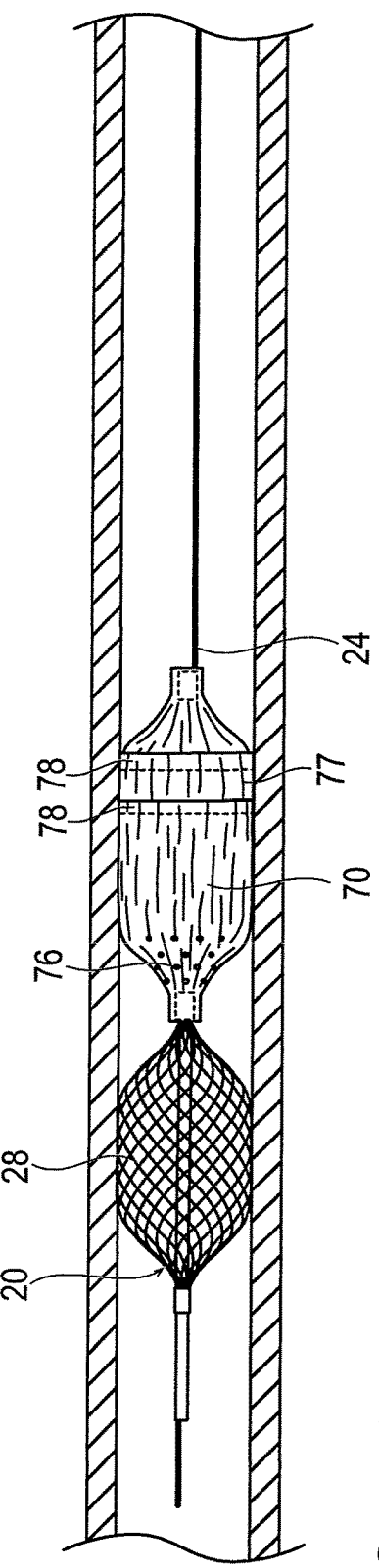

After the suction of the thrombus fragments 301 has been completed, the rotation and reciprocation of the shaft outer tube 111 and the shaft inner tube 112 are stopped. As illustrated in FIG. 20B, the outermost sheath member 120 is moved in the axial forward or distal direction so that the stirring unit 113 is positioned inside the outermost sheath member 120. After this, as illustrated in FIG. 21A, the removing device 100 is removed from the blood vessel while the expanding unit 20 is left in the blood vessel.

Figure 21B:
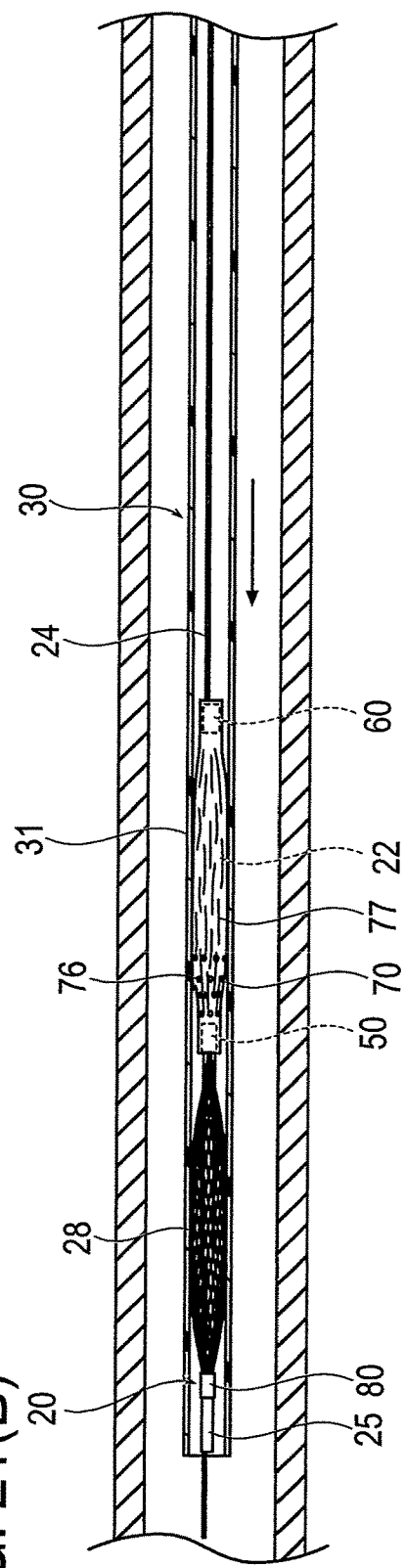

Next, the proximal end portion of the wire 24 is inserted into the sheath 30, and the sheath 30 is inserted into the blood vessel along the wire 24 and moved to a location near the first expanding member 22 and the cover 70. Next, as illustrated in FIG. 21B, the operator pushes the sheath 30 while holding the proximal portion of the wire 24 so that the wire 24 does not move in the axial direction, thereby moving the first expanding member 22, the second expanding member 28, and the cover 70 into the sheath 30 while reducing the outer diameters of the first expanding member 22, the second expanding member 28, and the cover 70. When the outer diameter of the cover 70 is reduced, the blood in the cover 70 is discharged from the cover 70 through the holes 76. When the cover 70 is moved into the sheath 30, the thrombus fragments 301 that have adhered to the cover 70 are also moved into the sheath 30. The second expanding member 28 and the cover 70 that are in contact with the inner wall surface of the blood vessel may be moved toward the proximal side so as to scrape off portions of the thrombus 300 on the inner wall surface of the blood vessel with the second expanding member 28 and the cover 70, and the portions of the thrombus 300 may then be moved into the sheath 30 together with the second expanding member 28 and the cover 70. After this, the expanding unit 20 and the sheath 30 are both removed from the blood vessel, and the treatment is completed.

As described above, the medical device 10 according to the present embodiment, which is a device to be inserted into a body lumen to obstruct flow in the body lumen, includes the shaft unit 23 that has an elongated shape; the proximal slider 50 that is slidably coupled to the shaft unit 23; the distal slider 80 that is slidably coupled to the shaft unit 23 and located further toward the distal side than the proximal slider 50; the first expanding member 22 that is an elastically deformable tube including a plurality of openings 21A, the first expanding member 22 including a distal portion coupled to the proximal slider 50 and a proximal portion coupled to the shaft unit 23, the tube including a central portion having an outer diameter greater than an outer diameter of both end portions of the tube in a natural state in which no external force is applied; the second expanding member 28 that is an elastically deformable tube including a plurality of openings 21A, the second expanding member 28 including a distal portion coupled to the distal slider 80 and a proximal portion coupled to the proximal slider 50 or the shaft unit 23, the tube including a central portion having an outer diameter greater than an outer diameter of both end portions of the tube in the natural state in which no external force is applied; and the cover 70 that surrounds the outer periphery of the first expanding member 22 and that is coupled to the proximal portion of the first expanding member 22, the proximal coupling member 60, which is located further toward the proximal side than the proximal portion of the first expanding member 22 and coupled to the shaft unit 23, or the shaft unit 23, the cover 70 being tubular and flexibly deformable independently of the first expanding member 22.

In the medical device 10 having the above-described structure, when the first expanding member 22, the second expanding member 28, and the cover 70 are moved out of the sheath 30, the first expanding member 22 and the second expanding member 28 expand in accordance with the shape of the body lumen due to the elastic force of the first expanding member 22 and the second expanding member 28. Accordingly, the first expanding member 22 presses the cover 70 against the inner wall surface of the body lumen, and the second expanding member 28, which is not surrounded by the cover 70, expands due to the elastic force of the second expanding member 28 so as to come into contact with the inner wall surface of the body lumen. Thus, the medical device 10 is able to obstruct flow in the body lumen with the cover 70, and can be appropriately secured to the body lumen because the second expanding member 28, which is not surrounded by the cover 70 and does not easily slip relative to the body lumen, comes into contact with the inner wall surface of the body lumen. In the medical device 10, the first expanding member 22, which presses the cover 70 against the inner wall surface of the body lumen to obstruct flow, and the second expanding member 28, which is not surrounded by the cover 70 and which is secured to the body lumen, are provided as separate components, and therefore the shapes of the expanding members 22 and 28 can be optimized in accordance with the functions thereof.

Accordingly, flow in the body lumen can be effectively obstructed and the medical device 10 can be appropriately secured to the body lumen.

The first expanding member 22 and the second expanding member 28 have different shapes in the radially expanded state. Accordingly, the first expanding member 22 may be formed in a shape suitable for pressing the cover 70 against the inner wall surface of the body lumen to obstruct flow in the body lumen, and the second expanding member 28 may be formed in a shape suitable for securing itself in the body lumen without slipping.

The second expanding member 28, which is not surrounded by with the cover 70, has an outer diameter greater than that of the first expanding member 22 in the natural state. Therefore, the second expanding member 28, which is not surrounded by the cover 70 to be secured to the body lumen, comes into tight contact with the inner wall surface of the body lumen and is effectively secured to the body lumen.

The distal end portion of the cover 70 is coupled to the proximal slider 50. Accordingly, in the medical device 10, since the length of first expanding member 22 in the axial direction decreases in the expanded state, the cover 70 may include the folded portions 77, which are folded so as to overlap themselves in the circumferential direction in such a manner that the inner surface of the cover 70 comes into contact with itself. When the cover 70 includes the folded portions 77, the contact area between the cover 70 and the inner wall surface of the body lumen increases, so that the contact force increases and blood flow can be effectively obstructed.

The medical device 10 includes the sheath 30, which is capable of accommodating the first expanding member 22, the second expanding member 28, and the cover 70 in the diameter-reduced state. Therefore, the first expanding member 22, the second expanding member 28, and the cover 70 in the diameter-reduced state can be carried to a desired location through a thin body lumen while being disposed in the sheath 30.

The medical device 10 further includes the pressing shaft 40, which is a tube that is disposed in the sheath 30 and through which the shaft unit 23 extends. The pressing shaft 40 has an inner diameter such that the first expanding member 22 and the cover 70 in the sheath 30 cannot pass through the pressing shaft 40. The pressing shaft 40 pushes the first expanding member 22, the second expanding member 28, and the cover 70 out of the sheath 30. By using the pressing shaft 40, the first expanding member 22, the second expanding member 28, and the cover 70 can be relatively easily pushed out of the sheath 30.

This disclosure also provides a treatment method for removing an object generated in a lesion in a body lumen by suction by using the above-described medical device 10. The method includes pushing the first expanding member 22, the second expanding member 28, and the cover 70 out of the sheath 30 to a location downstream of the lesion in the body lumen and causing the second expanding member 28 to expand due to the elastic force of the second expanding member 28 so that the second expanding member 28 is secured to the body lumen; causing the first expanding member 22 and the second expanding member 28 to expand due to the elastic force of the first expanding member 22 and the second expanding member 28 so that the expanding member that is not surrounded by the cover 70 (second expanding member 28 in the present embodiment) comes into contact with the inner wall surface of the body lumen and the expanding member that is surrounded by the cover 70 (first expanding member 22 in the present embodiment) presses the cover 70 against the inner wall surface of the body lumen; breaking up or dissolving the object generated in the lesion in the body lumen; inserting the device 100, which includes a suction hole that enables suction, into the body lumen and sucking up the object that has been broken or dissolved; causing the first expanding member 22, the second expanding member 28, and the cover 70 to contract; and removing the medical device 10 from the body lumen. With the above-described treatment method, flow in the body lumen can be obstructed by the cover 70 that is pressed against the inner wall surface of the body lumen by the first expanding member 22, and the second expanding member 28, which is not surrounded by the cover 70 and does not easily slip relative to the body lumen, comes into contact with the inner wall surface of the body lumen so that the second expanding member 28 can be appropriately secured to the body lumen. The first expanding member 22, which presses the cover 70 against the inner wall surface of the body lumen to obstruct flow, and the second expanding member 28, which is not surrounded by the cover 70 and which is secured to the body lumen, are provided as separate components, and therefore the structures of the expanding members 22 and 28 can be optimized in accordance with the functions thereof. Accordingly, flow in the body lumen can be effectively obstructed and the medical device 10 can be appropriately secured to the body lumen.

The present invention is not limited to the above-described embodiment, and various modifications can be made by a person skilled in the art within the technical idea of the present invention. For example, although the medical device 10 is moved toward the affected area from a location upstream of the affected area in the present embodiment, the medical device 10 may instead be moved toward the affected area from a location downstream of the affected area. When the medical device 10 is moved toward the affected area located at an upstream side (peripheral side) from a location downstream of (on the lung side of) the affected area, the medical device 10 moves to the affected area against the flow of blood. After the medical device 10 reaches the affected area, the first expanding member 22 and the second expanding member 28 are expanded. Since the blood flow is obstructed, the diameter of the blood vessel at the downstream side becomes smaller than that at the upstream side. Accordingly, the distance between the opening 160 and the inner wall surface of the blood vessel decreases, and thrombi in the affected area can be easily sucked up.

In the present embodiment, the removing device 100 including the stirring unit 113 is used to break up the thrombus 300. However, the medical device 10 may instead be used to effectively dissolve the thrombus with a thrombolytic agent instead of breaking up the thrombus 300. When the blood flow is obstructed by the medical device 10, the thrombus can be effectively dissolved by causing the thrombolytic agent to remain around the thrombus.

The body lumen into which the medical device 10 is inserted is not limited to a blood vessel, and may instead be, for example, a vein, a ureter, a bile duct, an oviduct, or a hepatic duct. The removing device is not limited to those having the above-described structure.

Figure 22A:
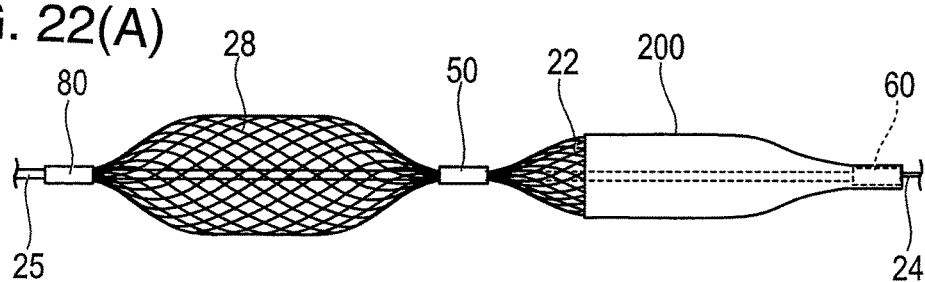
FIGS. 22A to 22D are plan views illustrating modifications of the expanding members and the cover of the expanding unit.

As in a modification illustrated in FIG. 22A, a cover 200 may include a proximal end portion coupled to the proximal coupling member 60 and a distal end portion disposed on a portion of the first expanding member 22 that expands. In this case, the volume of the cover 200 decreases, so that the cover 200 does not occupy a large space in the sheath 30 and the sliding resistance thereof decreases. Accordingly, the cover 200 can be easily moved out of and into the sheath 30. This structure allows blood to easily flow into the cover 200, and it is not necessary to form holes in the cover 200.

Figure 22B:
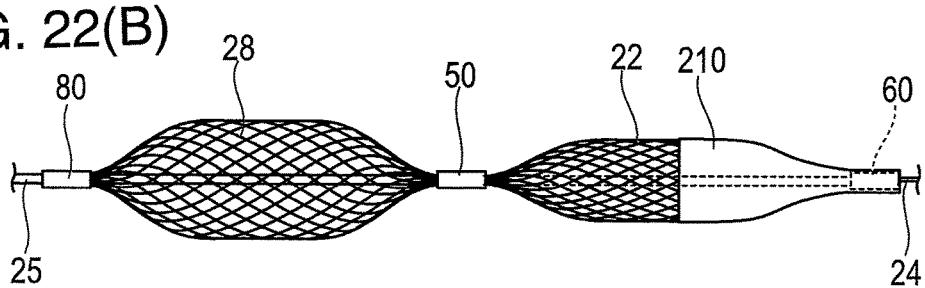

As in a modification illustrated in FIG. 22B, a cover 210 may include a proximal end portion coupled to the proximal coupling member 60, and the length of the cover 210 may be shorter than or equal to half the length of the first expanding member 22 in the axial direction in the expanded state. In such a case, the volume of the cover 210 can be further reduced and the cover 210 can be more easily moved out of and into the sheath 30.

Figure 22C:
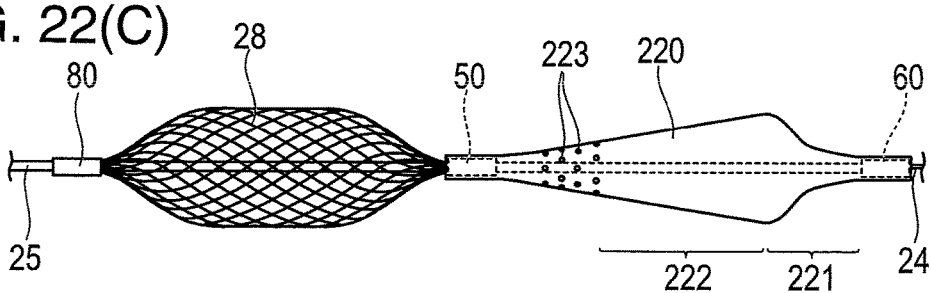

As in a modification illustrated in FIG. 22C, a cover 220 may include a proximal end portion coupled to the proximal coupling member 60; a proximal tapered portion 221, which has an outer diameter that increases toward the distal side (distal end or distal direction) from the proximal coupling member 60; and a distal tapered portion 222, which has an outer diameter that decreases toward the distal side from the proximal tapered portion 221. The distal tapered portion 222 is a portion that comes into contact with the inner wall surface of the body lumen. The cover 220 has holes 223 through which blood flows when the volume of inside of the cover 220 changes. Since the distal tapered portion 222 of the cover 220, which comes into contact with the inner wall surface of the body lumen, is tapered so that the diameter thereof decreases toward the distal side, when the cover 220 expands, the distal tapered portion 222 gradually comes into contact with the inner wall surface of the body lumen from a portion having a large outer diameter. This reduces the risk that two portions of the cover 220 that are apart from each other in the axial direction will come into contact with the inner wall surface of the body lumen, and a reduction in the effect of obstructing fluid flow can be suppressed. The cover 220 may have folded portions in the expanded state. It is not necessary that the distal end portion of the cover 220 extend to the proximal slider 50, and the distal end portion of the cover 220 may instead be disposed on a portion of the first expanding member 22 that expands.

Figure 22D:
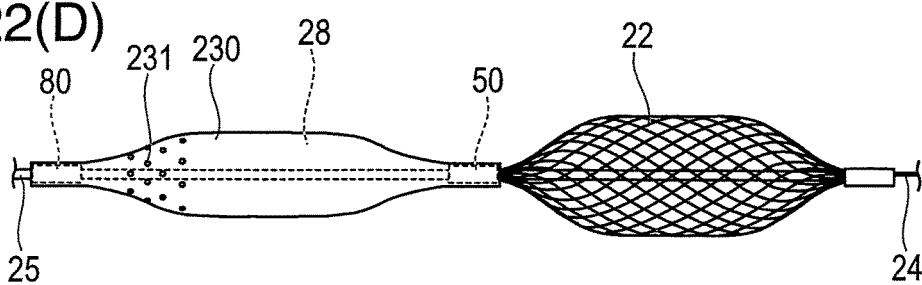

As in a modification illustrated in FIG. 22D, a cover 230 may be provided so as to surround the second expanding member 28 instead of the first expanding member 22. The cover 230 includes a distal end portion coupled to the distal slider 80 and a proximal end portion coupled to the proximal slider 50. The proximal end portion of the cover 230 may be secured to the proximal portion of the second expanding member 28. The distal end portion of the cover 230 may instead be disposed on a portion of the second expanding member 28 that expands. The cover 230 has holes 231 through which blood flows when the volume of the inside the cover 230 changes. The cover 230 may have folded portions in the expanded state.

At least a portion of the proximal slider 50, the proximal coupling member 60, and the wires 21 and 29 may be made of a material containing a radiopaque material. For example, portions of the wires 21 and 29 may be made of a material containing a radiopaque material. In such a case, the position of the medical device 10 can be appropriately determined by radiography, and the medical device 10 can be more easily manipulated. Preferred examples of the radiopaque material include gold, platinum, platinum-iridium alloys, silver, stainless steel, molybdenum, tungsten, tantalum, palladium, and alloys thereof.

The detailed description above describes embodiments of a medical device and treatment method representing examples of the inventive medical device and treatment method disclosed here. The invention is not limited, however, to the precise embodiment and variations described.

Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device to be inserted into a body lumen to obstruct flow in the body lumen, the medical device comprising:
    an elongated shaft;
    a proximal slider slidably coupled to the elongated shaft so that the proximal slider is slidable along the elongated shaft;
    a distal slider slidably coupled to the elongated shaft so that the distal slider is slidable along the elongated shaft, the distal slider being located distal of the proximal slider;
    a first expanding member that is an elastically deformable tube including a plurality of through openings, the first expanding member including a distal portion coupled to the proximal slider and a proximal portion coupled to the elongated shaft, the tube including a central portion possessing an outer diameter greater than an outer diameter of both end portions of the tube in a natural state in which no force is applied to the first expanding member;
    a second expanding member that is an elastically deformable tube including a plurality of through openings, the second expanding member including a distal portion coupled to the distal slider and a proximal portion coupled to the proximal slider, the tube of the second expanding member including a central portion having an outer diameter greater than an outer diameter of both end portions of the tube of the second expanding member in the natural state in which no force is applied to the second expanding member; and
    a cover that surrounds an outer periphery of one of the first and second expanding members and that is coupled to the proximal portion of the one of the first and second expanding members, to the proximal slider located further toward a proximal side than the proximal portion of the one of the first and second expanding members, or to the elongated shaft, the cover being tubular and flexibly deformable independently of the one of the first and second expanding members.

2. The medical device according to claim 1, wherein the first and second expanding members have different shapes in a radially expanded state.

3. The medical device according to claim 2, wherein the other of the first and second expanding members is not surrounded by any cover and has an outer diameter greater than an outer diameter of the one of the first and second expanding members in the natural state.

4. The medical device according to claim 1, wherein the cover includes a distal end portion coupled to the distal slider or the proximal slider.

5. The medical device according to claim 1, wherein the cover includes a distal end portion located radially outside an expandable portion of the one of the first and second expanding members, the distal end portion of the cover surrounding the expandable portion of the one of the first and second expanding members.

6. The medical device according to claim 1,
    wherein the cover includes
        a proximal tapered portion having an inner diameter that increases toward a distal end of the cover from a coupling portion at which the cover is coupled to the one of the first and second expanding members or to a member located proximally of a proximal end of the one of the first and second expanding members, and
        a distal tapered portion having an inner diameter that decreases toward the distal end from the proximal tapered portion.

7. The medical device according to claim 1, further comprising a sheath configured to accommodate the first and second expanding members and the cover in a diameter-reduced state.

8. The medical device according to claim 1, wherein the cover includes a plurality of through holes.

9. A medical device sized to be inserted into a body lumen to obstruct liquid flow in the body lumen, the medical device comprising:
    an elongated shaft;
    a first expanding member comprised of an expandable and contractable first tube configured to be radially outwardly expanded and radially inwardly contracted, the expandable and contractable first tube including a plurality of through openings;
    the expandable and contractable first tube including end portions at opposite axial ends of the expandable and contractable first tube, the elongated shaft passing through the expandable and contractable first tube so that the end portions of the expandable and contractable first tube surround the elongated shaft, at least one of the end portions of the expandable and contractable first tube being axially movable relative to the elongated shaft;
    the expandable and contractable first tube including a central portion possessing an outer diameter greater than an outer diameter of both end portions of the expandable and contractable first tube in a natural state in which no force is applied to the expandable and contractable first tube;
    a second expanding member configured to be radially outwardly expanded into contact with an inner surface of the body lumen and radially inwardly contracted out of contact with the inner surface of the body lumen, the expandable and contractable second tube including a plurality of through openings;
    the expandable and contractable second tube including end portions at opposite axial ends of the expandable and contractable second tube, the elongated shaft passing through the expandable and contractable second tube so that the end portions of the expandable and contractable second tube surround the elongated shaft, at least one of the end portions of the expandable and contractable second tube being axially movable relative to the elongated shaft;
    the expandable and contractable second tube including a central portion possessing an outer diameter greater than an outer diameter of both end portions of the expandable and contractable second tube in a natural state in which no force is applied to the expandable and contractable second tube;
    the central portion of the expandable and contractable first tube and the central portion of the expandable and contractable second tube being axially spaced apart from one another;
    a cover surrounding an outer periphery of the central portion of the expandable and contractable first tube so that when the expandable and contractable first tube is radially outwardly expanded, the cover is outwardly expanded into contact with the inner surface of the body lumen to obstruct liquid flow past the expandable and contractable first tube; and the central portion of the expandable and contractable second tube being devoid of any cover.

10. The medical device according to claim 9, wherein the elongated shaft possesses a distal end, the expandable and contractable second tube being positioned distal of the expandable and contractable first tube.

11. The medical device according to claim 9, wherein one of the end portions of the expandable and contractable first tube is axially movable relative to the elongated shaft, and the other one of the end portions of the expandable and contractable first tube is axially fixed relative to the elongated shaft.

12. The medical device according to claim 9, wherein the cover includes a plurality of through holes.

13. The medical device according to claim 9, further comprising:

a first slider slidably mounted on the elongated shaft so that the first slider is slidable along the elongated shaft;

a second slider slidably mounted on the elongated shaft so that the second slider is slidable along the elongated shaft, the second slider being located distal of the first slider;

the end portions of the expandable and contractable first tube including a distal end portion coupled to the first slider and a proximal end portion fixed in place relative to the elongated shaft; and the end portions of the expandable and contractable second tube including a distal end portion coupled to the second slider and a proximal end portion coupled to the first slider, the distal end portion of the expandable and contractable second tube being located distal of the proximal end portion of the expandable and contractable second tube.

14. The medical device according to claim 9, wherein the expandable and contractable second tube is located distal of the expandable and contractable first tube, the two end portions of the expandable and contractable second tube including a proximal end portion and a distal end portion, the proximal end portion of the expandable and contractable second tube being positioned proximal of the distal end portion of the expandable and contractable second tube, the proximal end portion of the expandable and contractable second tube being fixed to the elongated shaft by a proximal coupling member possessing an outer diameter, the medical device further comprising a pressing shaft possessing a lumen whose inner diameter permits the elongated shaft to be positioned in the inner lumen, the inner diameter of the lumen in the pressing shaft being smaller than the outer diameter of the proximal coupling member.

15. The medical device according to claim 9, wherein the cover surrounds an entire axial extent of the expandable and contractable first tube.

* * * * *